US010105319B2

(12) United States Patent
Riel

(10) Patent No.: US 10,105,319 B2
(45) Date of Patent: *Oct. 23, 2018

(54) SUSTAINED-RELEASE FORMULATIONS OF COLCHICINE AND METHODS OF USING SAME

(71) Applicant: Murray and Poole Enterprises Limited, Gibraltar (GB)

(72) Inventor: Susanne Riel, Dubai (AE)

(73) Assignee: Murray and Poole Enterprises Limited (GI)

( * ) Notice: Subject to any disclaimer, the term of this patent is extended or adjusted under 35 U.S.C. 154(b) by 0 days.

This patent is subject to a terminal disclaimer.

(21) Appl. No.: 14/563,503

(22) Filed: Dec. 8, 2014

(65) Prior Publication Data

US 2015/0094322 A1 Apr. 2, 2015

Related U.S. Application Data

(63) Continuation-in-part of application No. PCT/IB2014/001201, filed on Apr. 16, 2014.

(60) Provisional application No. 61/812,514, filed on Apr. 16, 2013.

(30) Foreign Application Priority Data

Nov. 26, 2013 (EP) ..................................... 13194505

(51) Int. Cl.

| A01N 43/54 | (2006.01) |
|---|---|
| A61K 31/505 | (2006.01) |
| A61K 9/20 | (2006.01) |
| A61K 31/165 | (2006.01) |
| A61K 45/06 | (2006.01) |
| A61K 47/02 | (2006.01) |
| A61K 47/12 | (2006.01) |
| A61K 47/26 | (2006.01) |
| A61K 47/36 | (2006.01) |
| A61K 47/38 | (2006.01) |

(52) U.S. Cl.
CPC .......... *A61K 9/2054* (2013.01); *A61K 9/2009* (2013.01); *A61K 9/2013* (2013.01); *A61K 9/2018* (2013.01); *A61K 9/2059* (2013.01); *A61K 9/2095* (2013.01); *A61K 31/165* (2013.01); *A61K 45/06* (2013.01); *A61K 47/02* (2013.01); *A61K 47/12* (2013.01); *A61K 47/26* (2013.01); *A61K 47/36* (2013.01); *A61K 47/38* (2013.01)

(58) Field of Classification Search
None
See application file for complete search history.

(56) References Cited

U.S. PATENT DOCUMENTS

| 3,173,876 | A | 3/1965 | Zobrist |
|---|---|---|---|
| 3,276,586 | A | 10/1966 | Rosaen |
| 3,541,005 | A | 11/1970 | Strathmann et al. |
| 3,541,006 | A | 11/1970 | Bixler et al. |
| 3,546,142 | A | 12/1970 | Michaels et al. |
| 4,285,987 | A | 8/1981 | Ayer et al. |
| 8,415,395 | B1 | 4/2013 | Davis et al. |
| 2002/0015735 | A1 | 2/2002 | Hedden |
| 2006/0171948 | A1 | 8/2006 | Weinstein et al. |
| 2006/0286108 | A1 | 12/2006 | Bell |
| 2008/0039408 | A1 | 2/2008 | Freudenberger |
| 2009/0093548 | A1 | 4/2009 | Davis et al. |
| 2009/0170952 | A1* | 7/2009 | Davis et al. ................. 514/613 |
| 2009/0299155 | A1 | 12/2009 | Yang |
| 2009/0312430 | A1 | 12/2009 | Sun et al. |
| 2011/0046227 | A1 | 2/2011 | Davis |
| 2011/0046228 | A1 | 2/2011 | Davis |
| 2011/0190397 | A1 | 8/2011 | Davis |
| 2015/0094322 | A1 | 4/2015 | Riel |
| 2015/0094323 | A1 | 4/2015 | Riel |

FOREIGN PATENT DOCUMENTS

| CN | 1939290 A | 4/2007 |
|---|---|---|
| CN | 101485637 A | 7/2009 |
| CN | 101485638 A | 7/2009 |
| CN | 101536990 A | 9/2009 |
| CN | 101732274 A | 6/2010 |
| JP | 2000034224 A | 2/2000 |
| JP | 2005523885 A | 8/2005 |
| JP | 2011140498 A | 7/2011 |

(Continued)

OTHER PUBLICATIONS

Zema et al., "Different HPMC Viscosity Grades as Coating Agents for an Oral Time and/or Site-Controlled Delivery System: An Investigation into the Mechanisms Governing Drug Release," Journal of Pharmaceutical Sciences, vol. 96, No. 6, Jun. 2007.*
Written Opinion and International Search Report for PCT Application No. PCT/IB2014/001201 dated Nov. 13, 2014.
Adler, Y., et al., "Colchicine treatment for recurrent pericarditis: a decade of experience," Circulation, Jun. 2, 1998, vol. 27, pp. 2183-2185.
Finkelstein, Y., et al., "Colchicine for the Prevention of Postpericardiotomy Syndrome," Herz, Dec. 2002, pp. 791-794, vol. 27, No. 8.
Imazio, M., et al., "Colchicine as First-Choice Therapy for Recurrent Pericarditis," Arch. Intern Med, 2005, pp. 1987-1991, vol. 165, No. 17.

(Continued)

*Primary Examiner* — Jared Barsky
(74) *Attorney, Agent, or Firm* — Biopharma Law Group, PLLC; Joanna Brougher; Thomas Siepmann

(57) ABSTRACT

Pharmaceutical compositions of colchicine for once-a-day oral administration are provided. The formulations comprise a sustained-release component and an optional immediate-release component, the compositions of which can be selectively adjusted, respectively, to release the active ingredient along a pre-determined or desired release profile. Methods of treating or preventing cardiovascular disease and/or inflammatory disease in mammalian subjects comprising the administration of the novel formulations disclosed herein are also provided.

14 Claims, 9 Drawing Sheets

(56) References Cited

FOREIGN PATENT DOCUMENTS

| JP | 2012519725 A | 8/2012 |
| JP | 2012236846 A | 12/2012 |
| JP | 2013510873 A | 3/2013 |
| WO | 1992015282 A2 | 9/1992 |
| WO | 2007048004 A2 | 4/2007 |
| WO | 2008131192 A2 | 10/2008 |
| WO | 2010046628 A1 | 4/2010 |

OTHER PUBLICATIONS

Imazio, M., et al., "Colchicine in Addition to Conventional Therapy for Acute Pericarditis," Circulation, 2005, pp. 2012-2016, vol. 112, No. 13.

Imazio, M., et al., "Colchicine for the Prevention of the Post-pericardiotomy Syndrome (COPPS): a multicenter, randomized, double-blind, placebo-controlled trial," European Heart Journal, 2010, pp. 2749-2754, vol. 31.

Imazio, M., et al., "Colchicine prevents early postoperative pericardial and pleural effusions," American Heart Journal, Sep. 2011, pp. 527-532, vol. 162, No. 3.

Imazio, M., et al., "Colchicine for recurrent pericarditis (CORP): a randomized trial," Ann. Intern. Med., Oct. 4, 2011, pp. 409-414, vol. 155 (No. 7).

Maisch, B., et al., "Guidelines on the Diagnosis and Management of Pericardial Diseases," European Heart Journal, 2004, pp. 916-928.

Nidorf, S., et al., "Low-Dose Colchicine for Secondary Prevention of Cardiovascular Disease," Journal of the American College of Cardiology, 2013, pp. 404-410, vol. 61, No. 4.

Siepmann, J., et al., "Predicting drug release from HPMC/lactose tablets", International Journal of Pharmaceutics, Jan. 1, 2013, pp. 826-834, vol. 144, No. 1-2.

Malonne et al., "Pharmacokinetic evaluation of a new oral sustained release dosage form of tramadol," Brit. J. Pharmacol., 57(3):270-278, 2003.

Lee et al., "Pharmacokinetic comparison of sustained- and immediate-release oral formulations of cilostazol in healthy Korean subjects: a randomized, open-label, 3-part, sequential, 2-period, crossover, single-dose, food-effect, and multiple-dose study," Clin. Ther., 33(12):2038-53, 2011.

Marcher, U., "Retalac, a new excipient for direct compression of sustained release formulations," http://www.pharmtech.com/meggle, Meggle, Jul. 9, 2010.

Nidorf et al., "Low-dose colchicine for secondary prevention of cardiovascular disease," (The LoDoCo Trial) ACTR No. ACTR12610000293066, ethics approval at QII Jul. 2008.

Antonopoulis et al., "Statins as Anti-inflammatory agents in Atherogenesis: Molecular mechanisms and lessons from the recent clinical trials," Curr. Pharma. Design, 18:1519-1530, 2012.

Gabrielyan et al., "Comparative effects of losartan and losartan colchicines combination therapy in unstable angina patients with hyperuricaemia", Eur. J. Echocardiography Abstracts Supplement, 516:S83, 2006.

Marcher, U., "Co-Processed Lactose-based excipients for Direct Compression," Meggle, Excipients & Technology, 2012.

Written Opinion and Search Report for PCT/AU2013/001261 dated Dec. 16, 2013.

International Preliminary report on Patentability for PCT/AU2013/001261 dated May 5, 2015.

Seferovic, P., et al., "Management Strategies in Pericardial Emergencies", Herz, 31:891-900, 2006.

Crittenden, D., et al., "Colchicine Use Is Associated with decreased prevalence of Myocardial Infarction in Patients with Gout," J. Rheumatol., 39:1458-1464, 2012.

Lagrue, G., et al., "Effect of colchicine on atherosclerosis—I. Clinical and biological studies" Clin. Physiol. Biochem. 3:221-225, 1985.

Raju, N., et al., Effect of colchicine compared with placebo on high sensitivity C-reactive protein in patients with acute coronary syndrome or acute stroke: a pilot randomized controlled trial,: J. Thrombosis and Thrombolysis, 33:88-94, 2011.

Nakamura, Y., et al., "Role of microtubules in ischemic preconditioning against myocardial infarction," Cardiovas. Res., 64:322-330, 2004.

O'Keefe Jr., J., et al., "Ineffectiveness of Colchicine for the prevention of Restenosis after coronary angioplasty," J. Am. Coll. Cardiol., 19:1597-1600, 1992.

Sparano, D.M. and R. Parker Ward, "Pericarditis and Pericardial Effusion: Management Update", Cardiovas. Med., 13:543-555, 2011.

Schlesinger, N., et al., "Canakinumab reduces the risk of acute gouty arthritis flares during initiation of allopurinol treatment: Results of a double-blind, randomized study", Animals Rheum. Dis. 70:1264-1271, 2011.

Judkins, C., et al., "LoDoCo: Low Dose Colchicine in stable coronary artery disease and the effect on hs-CRP and brachial flow mediated dilation," Heart Lung Circ., 20S:S1-S155, Abstract 89, 2011.

Kouroupis, R, et al., "From Colchicine and some of its derivatives to 1,2,3,9,10-Pentamethoxybenzo[alpha] heptalenes," Helv. Chimica Acta, 78:1247-1277, 1995.

Hufford, C.D., et al., "(13)C- and (1)H-NMR. Assignments for Colchicine Derivatives," Helv.Chimica Acta, 63:50-56, 1980.

Imazio et al., "Colchicine reduces postoperative atrial fibrillation: results of the Colchicine for the Prevention of the Postpericardiotomy Syndrome (COPPS) atrial fibrillation substudy," Circulation, 124(21)2290-2295, 2011.

* cited by examiner

SUSTAINED-RELEASE FORMULATIONS OF COLCHICINE AND METHODS OF USING SAME

CROSS-REFERENCE TO RELATED APPLICATIONS

This application is a continuation-in-part of PCT Application No. PCT/IB2014/001201, filed Apr. 16, 2014, which claims the benefit of U.S. Provisional Application No. 61/812,514, filed Apr. 16, 2013, and EP Patent Application No. 13194505.7, filed Nov. 26, 2013, the entire contents of which are incorporated herein by reference.

BACKGROUND OF THE INVENTION

Colchicine, chemical name (−)-N-[(7S,12aS)-1,2,3,10-tetramethoxy-9-oxo-5,6,7,9-tetrahydrobenzo[a]heptalen-7-yl]-acetamide, is an alkaloid found in extracts of *Colchicum autumnale*, *Gloriosa superba*, and other plants. It is a microtubule-disrupting agent used in the treatment of conditions that may be treated, relieved or prevented with anti-inflammatory treatment.

Colchicine is well recognized as a valid therapy in acute flares of gouty arthritis, familial Mediterranean fever (FMF), Behçet's disease. It has also been used to treat many inflammatory disorders prone to fibrosis. In the recent past, colchicine has been proposed to be effective in therapy in cardiovascular diseases.

In particular, colchicine has been proposed as a first treatment option for recurrent pericarditis (class I indication) and optional for acute pericarditis (class IIa indication) in the 2004 European guidelines on the management of pericardial diseases (Maisch et al., *Guidelines on the Diagnosis and Management of Pericardial Diseases*, Eur Heart J., 2004, 25, 916-928).

Imazio et al. (*Circulation*, 2005, 112 (13), 2012-2016) showed that colchicine was effective for the treatment and the prevention of recurrent pericarditis in a prospective, randomized, open-label designed study of 120 patients with a first episode of acute pericarditis (idiopathic, viral, post-pericardiotomy syndromes, and connective tissue diseases), who were randomly assigned to conventional treatment with aspirin or conventional treatment plus colchicine (1.0 to 2.0 mg for the first day and then 0.5 to 1.0 mg/day for 3 months). The primary end point was recurrence rate, which was significantly reduced from 32.3% down to 10.7% at 18 months in the colchicine group (p=0.004).

Further, the same group showed that colchicine could be efficient after conventional treatment failure to manage acute pericarditis (Imazio at al., *Arch InternMed*, 2005, 165 (17), 1987-91). In a prospective, randomized, open-label design, 84 consecutive patients with a first episode of recurrent pericarditis were randomly assigned to receive conventional treatment with aspirin alone or conventional treatment plus colchicine (1.0-2.0 mg the first day and then 0.5-1.0 mg/d for 6 months). The primary end point was the recurrence rate, which was significantly decreased in the colchicine group (actuarial rates at 18 months were 24.0% vs 50.6% with conventional treatment).

It has also been shown that colchicine is effective for secondary prevention of recurrent pericarditis Imazio et al., *Ann. Intern. Med.*, 2011, 155 (7), 409-14). Colchicine has also been proposed to reduce postpericardiotomy reactions revealed as pericarditis (Imazio et al., *Am. Heart J.*, 2011, 162 (3), 527-532; Meurin and Tabet, *Arch. Cardiovasc. Dis.*, 2011, 104 (8-9), 425-427).

Colchicine for the treatment of post-pericardiotomy syndrome (PPS) was tested for the first time in a preliminary prospective, open-label, randomized trial of colchicine (1.5 mg/day) compared with placebo beginning on the third post-operative day in 163 patients who underwent cardiac surgery (Finkelstein et al., *Herz*, 2002 27, 791-194).

The effectiveness of colchicine for the prevention of PPS has also been shown in a multicentre, double-blind, randomized trial, in which 360 patients (mean age 65.7+12.3 years, 66% males), 180 in each treatment arm, were randomized to receive placebo or colchicine (1.0 mg twice daily for the first day followed by a maintenance dose of 0.5 mg twice daily for 1 month in patients≥70 kg, and halved doses for patients, 70 kg or intolerant to the highest dose) on the third post-operative day (Imazio et al., *European Heart Journal*, 2010, 31, 2749-2754).

In another study, the effectiveness of colchicine has been shown for cardiovascular disease. In this clinical trial with a prospective, randomized, observer-blinded endpoint design, 532 patients with stable coronary disease receiving aspirin and/or clopidogrel (93%) and statins (95%) were randomly assigned colchicine 0.5 mg/day or no colchicine and followed for a median of 3 years (Nidorf et al., *JACC*, 2013, 61 (4), 404-410). This study showed that colchicine 0.5 mg/day administered in addition to statins and other standard secondary prevention therapies appeared effective for the prevention of cardiovascular events in patients with stable coronary disease.

For the treatment of gout, the recommended dose of colchicine (COLCRYS®) is 1.8 mg/day in one or multiple doses in one hour. For adults with gout, treatment is initiated with a dose of 1.2 mg at the first sign of symptoms followed by 0.6 mg one hour later. (Physician's Desk Reference, 68th ed., (2014)).

COLCRYS® is an immediate release formulation. Adverse effects associated with the administration of COLCRYS® include, but are not limited to, nausea, vomiting, abdominal pain, diarrhea, hair loss, weakness, nerve irritation, severe anemia, low white blood counts, and low platelets (Physician's Desk Reference, 68th ed., (2014)).

The instant invention addresses these and other needs by providing a modified formulation of colchicine characterized by a sustained release of an active ingredient. This invention additionally provides an effective, once-daily dosage form of colchicine or salts thereof, which may improve patient compliance and also may reduce some of the side effects of colchicine compared to the current or higher daily doses of immediate release colchicine formulations.

BRIEF SUMMARY OF THE INVENTION

According to aspects of the invention illustrated herein, there is provided a sustained release formulation of colchicine for use in preventing and/or treating a patient having cardiovascular disease, the formulation comprising: (a) colchicine or a pharmaceutically acceptable salt thereof in an amount of not more than 0.6 mg; (b) a retarding agent; and (c) at least one pharmaceutically acceptable excipient, wherein the formulation is administered to the patient once daily.

According to aspects of the invention illustrated herein, there is provided a sustained release formulation of colchicine for use in preventing and/or treating a patient having cardiovascular disease, the formulation comprising: (a) colchicine or a pharmaceutically acceptable salt thereof in an amount of about 0.55 mg; (b) lactose monohydrate in an amount of about 59 mg; (c) pregelatinized starch in an amount of about 7.5 mg; (d) Hypromellose in an amount of about 1.0 mg; (e) a retarding agent in an amount of about 25.0 mg; (f) talc in an amount of about 1.0 mg; and (g) stearic acid in an amount of about 1.0 mg, wherein the formulation is administered to the patient once daily.

BRIEF DESCRIPTION OF THE DRAWINGS/FIGURES

The patent or application file contains at least one drawing executed in color. Copies of this patent or patent application publication with color drawings will be provided by the Office upon request and payment of the necessary fee.

DETAILED DESCRIPTION OF THE INVENTION

I. Definitions

Figure 1:
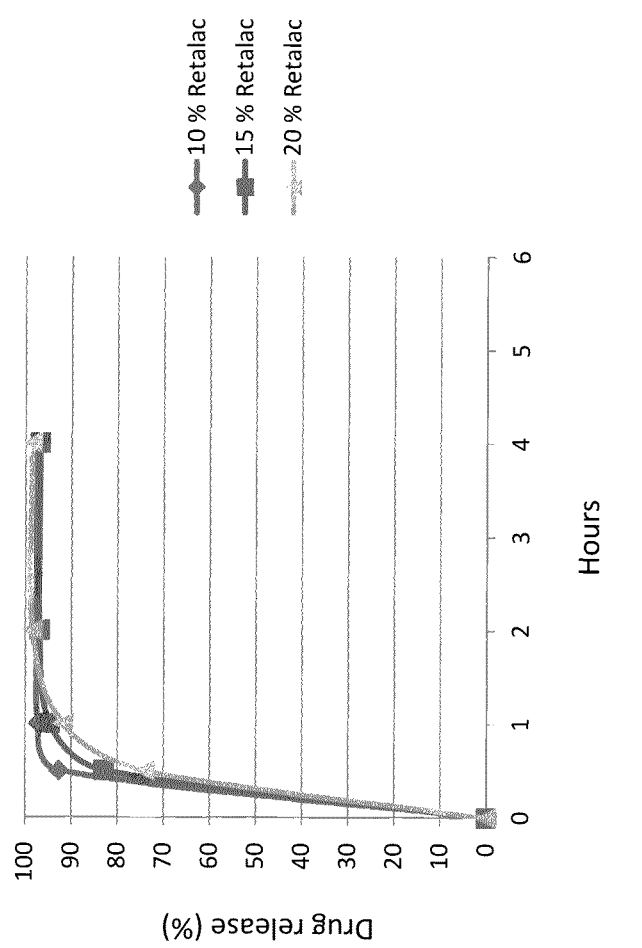
FIG. 1 shows the dissolution profiles for colchicine sustained-release formulations containing 10%, 15% and 20%, respectively, of an exemplary retarding agent.

For the purposes of this invention, the term "colchicine" includes colchicine or any pharmaceutically acceptable salts thereof.

"Pharmaceutically acceptable" means that which is generally safe, non-toxic and neither biologically nor otherwise undesirable and includes that which is acceptable for veterinary use as well as human pharmaceutical use.

"Pharmaceutically acceptable salts" includes derivatives of colchicine, wherein the colchicine is modified by making acid or base addition salts thereof, and further refers to pharmaceutically acceptable solvates, including hydrates, and co-crystals of such compounds and such salts. Examples of pharmaceutically acceptable salts include, but are not limited to, mineral or organic acid addition salts of basic residues such as amines; alkali or organic addition salts of acidic residues; and the like, and combinations comprising one or more of the foregoing salts. The pharmaceutically acceptable salts include non-toxic salts and the quaternary ammonium salts of the colchicine. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparaginate, glutamate, and the like; and combinations comprising one or more of the foregoing salts; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparaginate, glutamate, and the like; and combinations comprising one or more of the foregoing salts. All forms of such derivatives of colchicine are contemplated herein, including all crystalline, amorphous, and polymorph forms. Specific colchicine salts include colchicine hydrochloride, colchicine dihydrochloride, and co-crystals, hydrates or solvates thereof.

"Pharmacokinetic parameters" describe the in vivo characteristics of an active agent (or a metabolite or a surrogate marker for the active agent) over time, such as plasma concentration (C), Cmax, Cn, C24, Tmax, and AUC. "Cmax" is the measured plasma concentration of the active agent at the point of maximum, or peak, concentration. "Cmin" is the measured plasma concentration of the active agent at the point of minimum concentration. "Cn" is the measured plasma concentration of the active agent at about n hours after administration. "C24" is the measured plasma concentration of the active agent at about 24 hours after administration. The term "Tmax" refers to the time at which the measured plasma concentration of the active agent is the highest after administration of the active agent. "AUC" is the area under the curve of a graph of the measured plasma concentration of an active agent vs. time, measured from one time point to another time point. For example AUC0-t is the area under the curve of plasma concentration versus time from time 0 to time t, where t can be the last time point with measurable plasma concentration for an individual formulation. The AUC0-∞ or AUC0-INF is the calculated area under the curve of plasma concentration versus time from time 0 to time infinity. In steady-state studies, AUC0-τ is the area under the curve of plasma concentration over the dosing interval (i.e., from time 0 to time τ (tau), where tau is the length of the dosing interval. Other pharmacokinetic parameters are the parameter Ke or Kel, the terminal elimination rate constant calculated from a semi-log plot of the plasma concentration versus time curve; t1/2 the terminal elimination half-life, calculated as 0.693/Kel; CL/F denotes the apparent total body clearance after administration, calculated as Total Dose/Total AUC∞; and Varea/F denotes the apparent total volume of distribution after administration, calculated as Total Dose/(Total AUC∞×Kel).

"Efficacy" means the ability of an active agent administered to a patient to produce a therapeutic effect in the patient.

"Bioavailability" means the extent or rate at which an active agent is absorbed into a living system or is made available at the site of physiological activity. For active agents that are intended to be absorbed into the bloodstream, bioavailability data for a given formulation may provide an estimate of the relative fraction of the administered dose that is absorbed into the systemic circulation. "Bioavailability" can be characterized by one or more pharmacokinetic parameters.

A "dosage form" means a unit of administration of an active agent. Examples of dosage forms include tablets, capsules, injections, suspensions, liquids, emulsions, creams, ointments, suppositories, inhalable forms, transdermal forms, and the like.

An "immediate release formulation" refers to a formulation that releases greater than or equal to about 80% of the pharmaceutical agent in less than or equal to about 30 min.

For the purposes of this application, an enhancing agent ("enhancer") is defined as any non-pharmaceutically active ingredient that improves the therapeutic potential of a formulation.

"Sustained release" is defined herein as release of a pharmaceutical agent in a continuous manner over a prolonged period of time.

By "prolonged period of time" it is meant a continuous period of time of greater than about 1 hour, greater than about 4 hours, greater than about 8 hours, greater than about 12 hours, greater than about 16 hours, or up to more than about 24 hours.

As used herein, unless otherwise noted, "rate of release" or "release rate" or "dissolution rate" of a drug refers to the quantity of drug released from a dosage form per unit time, e.g., milligrams of drug released per hour (mg/hr) or a percentage of a total drug dose released per hour. Drug release rates for dosage forms are typically measured as an in vitro rate of drug release, i.e., a quantity of drug released from the dosage form per unit time measured under appropriate conditions and in a suitable fluid. The release rates referred to herein are determined by placing a dosage form to be tested in a medium in an appropriate dissolution bath. Aliquots of the medium, collected at pre-set intervals, are then injected into a chromatographic system fitted with an appropriate detector to quantify the amounts of drug released during the testing intervals.

Side effect is defined herein as a secondary and usually adverse effect of a drug.

Terms such as "treating" or "treatment" or "to treat" or "alleviating" or "to alleviate" refer to both 1) therapeutic measures that cure, slow down, lessen symptoms of, reverse, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on. The meaning of the terms "eukaryote", "animal", "mammal", etc. is well known in the art and can, for example, be deduced from Wehner und Gehring (1995; Thieme Verlag). In the context of this invention, it is also envisaged that animals are to be treated which are economically, agronomically or scientifically important. Scientifically important organisms include, but are not limited to, mice, rats, and rabbits. Non-limiting examples of agronomically important animals are sheep, cattle and pigs, while, for example, cats and dogs may be considered as economically important animals. In one embodiment, the subject/patient is a mammal; in another embodiment, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orang-utan, a gibbon, a sheep, cattle, or a pig); most preferably, the subject/patient is a human.

II. Colchicine

In the following, colchicine used according to the present invention will be described in detail. The chemical structure of colchicine (ChemID 2012) is as follows:

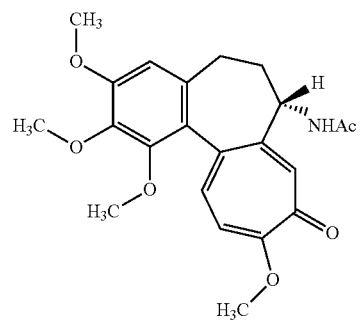 [SMILES: COc1cc2c(c(OC)c1OC)-c1ccc(OC)c(=O)cc1[C@@H](NC(C)=O)CC2]

The chemical name of colchicine is: N[5,6,7,9-tetrahydro-1,2,3,10-tetratmethoxy 9-oxobenzo[a]heptalen-7-yl],(S)-acetamide; molecular formula: $C_{22}H_{25}NO_6$; CAS number: 64-86-8.

Colchicine is an anti-inflammatory drug with a long history in human medicine, used for the symptomatic treatment of inflammatory diseases, most prominently gout. It is a natural product which can be extracted from two plants of the lily family, *Colchicum autumnale* and *Gloriosa superba*. Colchicine is a tricyclic alkaloid and has a molecular mass of 399.437. The active ingredient colchicine as well as its tablet formulation is listed in various national and international pharmacopeias such as the United States Pharmacopeia (USP).

The positive effect of its plant source in the treatment of rheumatism and swelling was described first already around 1500 B.C. in Egypt. Its use in gout was first described around 1500 years ago (Graham and Roberts, 1953, *Ann Rheum Dis* 12(1): 16-9). Today, the therapeutic value of colchicine is well established in a number of inflammatory diseases and approved by FDA for the prophylaxis and treatment of acute gout flares and familial Mediterranean fever (FMF). Other important established, though off-label uses are amongst others, Behçet's disease and recurrent pericarditis. In all known indications, it is generally administered orally as solid tablets in strengths of 0.5-0.6 mg/tablet (e.g. Europe and United States, respectively). The pharmacotherapeutic mechanism of action of colchicine in diverse disorders is not fully understood, though it is known that the drug accumulates preferentially in leucocytes, particularly neutrophils which is important for its therapeutic effect. Three major interactions of colchicine with specific proteins modulate its pharmacokinetics: tubulin, cytochrome P450 3A4 (CYP3A4), and P-glycoprotein. It is assumed that most therapeutic effects of the drug are related to its capacity to bind to β-tubulin, thus inhibiting self-assembly and polymerization of microtubules. Availability of tubulin is essential for several cellular functions such as mitosis. Therefore colchicine effectively functions as a "mitotic poison" or spindle poison. By inhibiting microtubule self-assembly, colchicine interferes with many cellular functions involved in the immune response such as modulation of the production of chemokines and prostanoids and inhibition of neutrophil and endothelial cell adhesion molecules. Eventually it decreases neutrophil degranulation, chemotaxis and phagocytosis, thus reducing the initiation and amplification of inflammation. Colchicine also inhibits uric acid crystal deposition (a process important to the genesis of gout), which is enhanced by a low pH in the tissues, probably by inhibiting oxidation of glucose and subsequent lactic acid reduction in leukocytes (Imazio, Brucato et al. 2009, *Eur Heart J,* 30(5): 532-9; Cocco, Chu et al. 2010, *Eur J Intern Med,* 21(6): 503-8; Stanton, Gernert et al. 2011, *Med Res Rev,* 31(3): 443-81). In the management of pericarditis, colchicine excerpts its therapeutic effect by suppressing the acute pericardial inflammation. However, the exact cellular and molecular mechanisms of how colchicine relieves pain and inflammation in acute pericarditis and prevents recurrences are not fully understood.

Colchicine in the context of the present invention can be used for the prevention and/or treatment of cardiovascular diseases and/or inflammatory diseases.

III. Sustained Release Formulations

The present invention additionally provides a sustained release colchicine formulation for the treatment or prevention of a cardiovascular disease and/or an inflammatory disorder in a subject wherein colchicine is released from the formulation at a sustained rate along a pre-determined or desired release profile. Such release is achieved by incorporation into the formulation of an extended release component and an optional immediate release component. The colchicine formulation of the present invention may be formulated in a dosage form selected from a tablet, a pill, a capsule, a caplet, a troche, a sachet, a cachet, a pouch, sprinkles, or any other form suitable for oral administration.

According to the present invention, colchicine as described herein (i.e., inter alia, in the form of a (pharmaceutical) composition) is administered in the form of a sustained release preparation. Other expressions like "extended release", "controlled release", "modified release" or "delayed release" "preparation" or "formulation" are understood herein to have the same meaning as "sustained release preparation". Such preparations can in principal be in any form conceivable to the skilled person and include pharmaceutical forms for oral (solid, semi-solid, liquid), dermal (dermal patch), sublingual, parenteral (injection), ophthalmic (eye drops, gel or ointment) or rectal (suppository) administration, as long as a sustained release is ensured. In some embodiments, the sustained release formulation is not a controlled release osmotic pump double layer tablet.

In accordance with the invention, sustained release preparations encompass all pharmaceutical forms that create a steady drug release profile making the drug substance available over an extended period of time following application to the patient. Such an extended period of time may be between 10, 20, 30, 40, 50 or 60 minutes and about 2, 3, 4, 5, 6, 7, 8, 9, 10, 11, 12, 13, 14, 15, 16, 17, 18, 19, 20, 21, 22, 23 or 24 hours. Extended release may also be defined functionally as the release of over 50, 55, 60, 65, 70, 75, 80, 85, 90, 95 or 99 percent (%) of colchicine after about 10, 20, 30, 40, 50 or 60 minutes and about 2, 3, 4, 5, 6, 7, 8, 9, 10, 11, 12, 13, 14, 15, 16, 17, 18, 19, 20, 21, 22, 23 or 24 hours. Extended release as used herein may also be defined as making colchicine available to the patient regardless of uptake, as some colchicine may never be absorbed by the patient. Various extended release dosage forms may be designed readily by one of skill in art as disclosed herein to achieve delivery and sustained release of colchicine to the liver and/or both the small and large intestines, to only the small intestine, or to only the large intestine.

In some embodiments, sustained release preparations may be pH independent. This allows such preparations to dissolve in almost any environment. In other embodiments, sustained release preparations may be pH dependent. This allows release to be accomplished at some generally predictable location in the lower intestinal tract more distal to that which would have been accomplished if there had been no delayed release alterations. A method for delay of release is, e.g., a coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. Polymers and compatible mixtures thereof may be used to provide the coating for the delayed or the extended release of active ingredients, and some of their properties, include, but are not limited to: shellac, also called purified lac, a refined product obtained from the resinous secretion of an insect. This coating dissolves in media of pH>7.

In some embodiments, sustained release preparations may be influenced by the presence of alcohol in the body. The presence of alcohol is a patient's body can increase dissolution of the composition and can cause immediate release of the entire dose. This effect is known as "dose dumping" and is dependent on the alcohol solubility of the materials. For sustained release preparations which contain a higher dose for slow release over 24 hours, for instance, this effect can have safety concerns and can even be life threatening.

To achieve a uniform or continuous rate of release, sustained release preparations may be prepared using time release hydrophilic matrices. These time release hydrophilic matrices are known in the field of drug formulations. For example, one such hydrophilic matrix is hydroxypropyl methylcellulose (HPMC) or Hypromellose. Hydrophilic matrices provide an initial release of the drug product in the initial phase mainly triggered by a rapid swelling of the surface of the matrix tablet, combined with an erosion process leading to an immediate release of the drug substance distributed close to the surface of the tablet. In an embodiment, about 50%, about 45%, about 40%, about 35%, about 30%, about 25%, about 20%, about 15%, or about 10% of the drug substance may immediately be released depending on the desired release profile. In an embodiment, at least about 20% of the drug substance may immediately be released. In another embodiment, at least about 20% of the drug substance may be released within about the first 30 minutes. As used herein, the term "about" or "approximately" refers to a variation of 10% from the indicated values (e.g., 50%, 45%, 40%, etc.), or in case of a range of values, means a 10% variation from both the lower and upper limits of such ranges. For instance, "about 50%" refers to a range of between 45% and 55%. Within the initial swelling of the tablet surface a gel formation of the hydrophilic matrix starts. This gelling prevents the tablet core from dissolving and disintegrating immediately, thereby allowing the main part of the drug substances to dissolve slowly over time within in this gel structure and diffuse into solution following the rules of Fick's law. The diffusion itself may be triggered in this formulation approach by the concentration of the Hypromellose and the viscosity of the formed gel, defined over the molecular weight of the Hypromellose. Therefore, drug release profiles can be modified by varying different viscosity grades of Hypromellose or mixtures thereof. All corresponding formulation and process parameters achieving the predicted release profile are common knowledge and can be adjusted using actual development technologies e.g. formulation screenings, statistical trials designs.

In an embodiment, the substance responsible for sustained release of the controlled-release formulation can further mix with a binder. The binder is added to increase the mechanical strength of the granules and tablets during formation. Binders can be added to the formulation in different ways: (1) as a dry powder, which is mixed with other ingredients before wet agglomeration, (2) as a solution, which is used as agglomeration liquid during wet agglomeration, and is referred to as a solution binder, and (3) as a dry powder, which is mixed with the other ingredients before compaction. In this form the binder is referred to as a dry binder. Solution binders are a common way of incorporating a binder into granules. In certain embodiments, the binder used in the formulation is in the form of a dry powder binder. Non-limiting examples of binders useful for the core include hydrogenated vegetable oil, castor oil, paraffin, higher aliphatic alcohols, higher aliphatic acids, long chain fatty acids, fatty acid esters, wax-like materials such as fatty alcohols, fatty acid esters, fatty acid glycerides, hydrogenated fats, hydrocarbons, normal waxes, stearic acid, stearyl alcohol, hydrophobic and hydrophilic polymers having hydrocarbon backbones, and mixtures thereof. Specific examples of water-soluble polymer binders include modified starch, gelatin, polyvinylpyrrolidone, cellulose derivatives (such as for example hydroxypropyl methylcellulose (HPMC) and hydroxypropyl cellulose (HPC)), polyvinyl alcohol and mixtures thereof. In an embodiment, the binder is HPMC. In another embodiment, the binder is Hypromellose 6 mPa*s. In an embodiment, the binder can be present in an amount of from about 1% to about 30% by weight of the formulation.

In another embodiment of the invention, the sustained release formulation may include a disintegrant. A disintegrant refers to an agent used in pharmaceutical preparation of tablets, which causes them to disintegrate and release their medicinal substances on contact with moisture. In an embodiment, the disintegrant may be water soluble to support the disintegrantation of a tablet in the stomach. Non-limiting examples of disintegrants for use in the formulation include sucrose, lactose, in particular lactose monohydrate, trehalose, maltose, mannitol and sorbitol, croscarmellose sodium, crospovidone, alginic acid, sodium alginate, methacrylic acid DVB, cross-linked PVP, microcrystalline cellulose, polacrilin potassium, sodium starch glycolate, starch, pregelatinized starch and mixtures thereof. In at least one embodiment the disintegrant is selected from microcrystalline cellulose (e.g. Avicel PH101), cross-linked polyvinylpyrrolidone (e.g. KOLLIDON® CL), cross-linked sodium carboxymethylcellulose (e.g. AC-DI-SOL™), starch or starch derivatives such as sodium starch glycolate (e.g. EXPLOTAB®), or combinations with starch (e.g. PRIMOJEL™), swellable ion-exchange resins, such as AMBERLITE™ IRP 88, formaldehyde-casein (e.g. ESMA SPRENG™), and mixtures thereof.

In another embodiment of the invention, the sustained release formulation may include a filling agent or filler. A filling agent refers to an inert substance used as filler to create desired bulk, flow properties, and compression characteristics in preparation of tablets. Non-limiting examples of filling agents for use in the formulation include sucrose, lactose, in particular lactose monohydrate, trehalose, maltose, mannitol and sorbitol, croscarmellose sodium, crospovidone, alginic acid, sodium alginate, methacrylic acid DVB, cross-linked PVP, microcrystalline cellulose, polacrilin potassium, sodium starch glycolate, starch, pregelatinized starch and mixtures thereof. In an embodiment, lactose monohydrate is included as a filling agent in an amount of about 10% to about 80%, preferably about 59%, by weight of the tablet. In an embodiment, pregelatinized starch is included as a filling agent in an amount of about 5% to about 50%, preferably about 7.5%, by weight of the tablet.

In another embodiment, the sustained release formulation of the present invention may include a release retarding agent for maintaining a uniform release rate of the drug. Examples of retarding agents include, but are not limited to, cellulose ethers, cellulose esters, acrylic acid copolymers, waxes, gums, glyceryl fatty acid esters and sucrose fatty acid esters. In one embodiment, the retarding agent is RETALAC® (Meggle), a spray agglomerated blend of 50 parts lactose monohydrate and 50 parts hypromellose. The viscosity of hypromellose used herein may range from 6 mPa*s-100,000 mPa*s. In an embodiment, the viscosity of hypromellose used is 4000 mPa*s. Adjusting the amount of retarding agent in the composition may alter the release rate of the drug. In one embodiment, the retarding agent of the formulation of the present invention releases colchicine in a continuous and uniform manner and is adjusted in such a way that about 80% of the active ingredient is released in vitro in the predetermined period of time. By way of example, and by no means limiting the scope of the invention, the period of time may be not more than 24 hours, not more than 16 hours, not more than 12 hours, not more than 8 hours, not more than 6 hours, not more than 4 hours, not more than 3.5 hours, or not more than 1.5 hours depending on desired attributes of the final product. It is understood that the release rate can vary based on whether the experiment is conducted in vitro or in vivo. Therefore, if the desired release rate is between about 1.5 to about 3.5 hours in vitro or between about 1.5 to about 6 hours in vitro, the release rate under in vivo conditions, depending on the experimental conditions, may actually be different. In an embodiment, the sustained release formulation of the present invention releases colchicine in a continuous and uniform manner in such a way that about 80% of the active ingredient is released in vitro in between about 1.5 and about 3.5 hours.

In another embodiment, the sustained release formulation of the present invention may include a glidant. A glidant can be used to improve powder flow properties prior to and during tableting and to reduce caking. Suitable glidants include colloidal silicon dioxide, magnesium trisilicate, powdered cellulose, talc, tribasic calcium phosphate and the like. In one embodiment, talc is included as a glidant in an amount of about 0.05% to about 5%, preferably about 1%, by weight of the tablet.

In another embodiment, the sustained release formulation of the present invention may include a lubricant. Lubricants can be added to pharmaceutical formulations to decrease any friction that occurs between the solid and the die wall during tablet manufacturing. High friction during tableting can cause a series of problems, including inadequate tablet quality (capping or even fragmentation of tablets during ejection, and vertical scratches on tablet edges) and may even stop production. Accordingly, lubricants are added to certain tablet formulations of the present invention including certain embodiments of the formulation described herein. Non-limiting examples of lubricants useful for the core include glyceryl behenate, stearic acid, hydrogenated vegetable oils (such as hydrogenated cottonseed oil (STEROTEX®), hydrogenated soybean oil (STEROTEX® HM) and hydrogenated soybean oil & castor wax (STEROTEX® K)), stearyl alcohol, leucine, polyethylene glycol (MW 1450, suitably 4000, and higher), magnesium stearate, glyceryl monostearate, polyethylene glycol, ethylene oxide polymers (for example, available under the registered trademark CARBOWAX® from Union Carbide, Inc., Danbury, Conn.), sodium lauryl sulfate, magnesium lauryl sulfate, sodium oleate, sodium stearyl fumarate, DL-leucine, colloidal silica, mixtures thereof and others as known in the art. In one embodiment, stearic acid is included as a lubricant in an amount of about 0.05% to about 5%, preferably about 1%, by weight of the tablet.

Sweeteners that can also be used in the taste-masking coating of certain embodiments of the matrix dosage forms include glucose (corn syrup), dextrose, invert sugar, fructose, and mixtures thereof (when not used as a carrier); saccharin and its various salts, such as sodium salt; dipeptide sweeteners such as aspartame; dihydrochalcone compounds, glycyrrhizin; *Steva Rebaudiana* (Stevioside); chloro derivatives or sucrose such as sucralose; and sugar alcohols such as sorbitol, mannitol, xylitol, and the like. Also contemplated are hydrogenated starch hydrolysates and the synthetic sweeteners such as 3,6-dihydro-6-methyl-1-1-1,2,3-oxathiazin-4-1-2,2-dioxide, particularly the potassium salt (acesulfame-K), and sodium and calcium salts thereof. The sweeteners can be used alone or in any combination thereof.

The controlled-release formulation of the present invention can further contain one or more pharmaceutically acceptable excipients such as granulating aids or agents, colorants, flavorants, pH adjusters, anti-adherents, glidants and like excipients conventionally used in pharmaceutical compositions. In an embodiment, a coloring excipient can be advantageously added as giving rise to visual change preventing abuse. It can color simultaneously the liquid or the particles or one independently of the other. Among suitable coloring excipients the following may be cited: indigotine, cochineal carminic acid, yellow orange S, allura red AC, iron oxides, cucurmin, riboflavin, tartrazine, quinoline yellow, azorubine, amaranth, carmines, erythosine, red 2G, patented blue V, glittering blue FCF, chlorophylls, copper complexes of chlorophylls, green S, caramel, glittering black BN, carbo medicinalis vegetabilis, brown FK and HT, carotenoids, Annatto extracts, paprika extracts, lycopene, lutein, canthaxanthin, beetroot red, anthocyanes, calcium carbonate, titanium dioxide, aluminium, silver, gold or litholrubin BK or any other coloring excipient suitable for an oral administration.

In an embodiment, a sustained release formulation may be coated. Coatings may provide a variety of functions. In some embodiments, coatings may be used, for example, to achieve delayed release, resistance to acid, targeted release in the lower GI tract, avoidance of bad taste in mouth. In some embodiments, coatings may be used to protect the API/tablet from light and provide for better mechanical resistance. Of course it should be appreciated that a coating may serve other functions as well and a person skilled in the art knows the purpose of tablet coating.

The pharmaceutical composition and/or the solid carrier particles can be coated with one or more enteric coatings, seal coatings, film coatings, barrier coatings, compress coatings, fast disintegrating coatings, or enzyme degradable coatings. Multiple coatings may be applied for desired performance. Further, one or more of the actives may be provided for immediate release, pulsatile release, controlled release, extended release, delayed release, targeted release, synchronized release, or targeted delayed release. In fact, the formulation may include combinations of typical pharmaceutical actives (e.g., pseudephedrin) and vitamins (e.g., Vitamin C), minerals (Ca, Mg, Zn, K) or other supplements (e.g., St. John's Wort, echinacae, amino acids). For release/absorption control, solid carriers can be made of various component types and levels or thicknesses of coats, with or without an active ingredient. Such diverse solid carriers can be blended in a dosage form to achieve a desired performance. The liquid formulations may be delivered to, and adapted for, oral, nasal, buccal, ocular, urethral, transmucosal, vaginal, topical or rectal delivery, although oral delivery is used mostly.

When formulated with microparticles or nanoparticles, the drug release profile can easily be adapted by adding a coating, e.g., a hard or soft gelatin coating, a starch coating, a resin or polymer coating and/or a cellulosic coating. Although not limited to microparticles or nanoparticles (as in, e.g., microcapsules or nanocapsules), such dosage forms may be further coated with, for example, a seal coating, an enteric coating, an extended release coating, or a targeted delayed release coating. The term "enteric coating" as used herein relates to a mixture of pharmaceutically acceptable excipients that is applied to, combined with, mixed with or otherwise added to the carrier or composition. The coating may be applied to an active that is compressed, molded or extruded and may also include: gelatin, and/or pellets, beads, granules or particles of the carrier or composition. The coating may be applied through an aqueous dispersion or after dissolving in appropriate solvent. The carrier may or may not be fully or partially biodegradable.

In an embodiment, polymethacrylate acrylic polymers can be employed as coating polymers. In at least one embodiment, the coating is an acrylic resin lacquer used in the form of an aqueous dispersion, such as that which is commercially available from Rohm Pharma under the trade name EUDRAGIT® or from BASF under the trade name KOLLICOAT®. In a more preferable embodiments, EUDRAGIT® E100 is used as the coating polymer, which is a cationic copolymer based on dimethylaminoethyl methacrylate and neutral methacrylic esters having a average molecular weight is approximately 150,000. Different coating polymers of the certain embodiments can be mixed together in any desired ratio in order to ultimately obtain a coating having a desirable drug dissolution profile. Coating methods can consist in spraying a solution of the polymer on the tablets, either in a pan coater or a fluid bed coating apparatus. The solvent may be organic or aqueous, depending on the nature of the polymer used. In a preferable embodiment, the solvent is alcohol. Coating methods are well known in the art.

The compositions of the present invention can also be formulated as enteric coated delayed release oral dosage forms, i.e., as an oral dosage form of a pharmaceutical composition as described herein that uses an enteric coating to effect release in the lower gastrointestinal tract. The enteric coated dosage form will generally include microparticles, microgranules, micropellets or microbeads of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

Carriers for use with the present invention include permeable and semipermeable matrices or polymers that control the release characteristics of the formulation. Such polymers include, for example, cellulose acylates, acetates, and other semi-permeable polymers such as those described in U.S. Pat. No. 4,285,987 (hereby incorporated by reference), as well as the selectively permeable polymers formed by the coprecipitation of a polycation and a polyanioni as disclosed in U.S. Pat. Nos. 3,173,876; 3,276,586; 3,541,005; 3,541,006 and 3,546,142 (relevant portions incorporated herein by reference).

Other carriers for use with the present invention include, e.g., starch, modified starch, and starch derivatives, gums, including but not limited to xanthan gum, alginic acid, other alginates, benitoniite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan (and derivatives), gum karaya, biosynthetic gum, etc. Other useful polymers include: polycarbonates (linear polyesters of carbonic acid); microporous materials (bisphenol, a microporous poly(vinylchloride), microporous polyamides, microporous modacrylic copolymers, microporous styrene-acrylic and its copolymers); porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone).

Additional additives and their levels, and selection of a primary coating material or materials will depend on the following properties: pH levels at target site, desirability to make tablet pH dependent or pH independent, solubility in alcohol, resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; easy application as a coating (substrate friendly); and economical practicality.

Further to the above, various formulations, not limiting the scope of the present invention, illustrating the invention are described hereafter. A controlled-release tablet or capsule or the like comprises colchicine as a core coated with an immediate release layer. A controlled-release double layer tablet or capsule or the like comprises a layer of sustained release and a layer of immediate release. A controlled-release tablet with more than two layers comprises (i) one or two more layers of substance controlling the sustained release and (ii) one or two more layers of immediate release.

According to one embodiment of the invention, the composition comprising colchicine is further coated with at least one release-slowing intermediate layer of slightly soluble intermediate layer to control release of colchicine.

Traditionally, colchicine immediate release dosage forms (mostly tablets, also injections or oral solutions) have been used in the treatment of gout or FMF. Worldwide, all approved pharmaceuticals containing colchicine are approved only for gout and/or FMF and are immediate release tablets. Colchicine can be used in the prevention of certain other inflammatory diseases such as pericarditis, PPS and, most recently, patients with stable coronary heart diseases. The difference between treatment and prevention with regard to colchicine is that in treatment, an overt disease and/or ongoing inflammation has to be treated. Thus high levels of colchicine are required, which usually goes hand in hand with unwanted side effects, most prominently gastrointestinal insults, as well as increased risk of toxicity. In prevention, one does not have to suppress ongoing inflammation but rather suppress an outbreak of inflammation. Thus, supposedly lower and steadier levels of colchicine are required and are beneficial. As described in the present invention, this is achieved by administering colchicine formulated as a sustained release preparation, as described above.

In the treatment of an acute inflammatory disease such as FMF or gout, high doses and high serum levels are necessary and desired to suppress inflammation. Therefore conventional tablets with a fast release and a rather low plasma half-life are suitable. However, in case of prevention of a cardiovascular disease, lower levels may be sufficient to inhibit neutrophil activity. The sustained release system facilitates more steady levels of colchicine and reduces the incidence of adverse events.

An advantage of colchicine administered as sustained release is, e.g., a flattening of the serum level curve (lower but broader peak levels) reduces the incidence of serious adverse events related to colchicine toxicity, also in case of potential drug interactions thereby increasing compliance. Much of colchicine related toxicity comes from the fact that one or both of the excretion pathways (liver and kidney) is reduced in its activity, either by other drugs or by a disease (e.g. kidney insufficiency). In the case of a slower and extended drug absorption (extended release), the body has also more time to excrete the colchicine from the system. In this case, it is less likely that colchicine levels reach toxic levels in case of defective excretion (due to drug interaction or disease). Another potential advantage of colchicine administered as a sustained release formulation is that plasma levels remain more evenly distributed (i.e., the variability of plasma levels, such as the differences in Cmax, Tmax, AUC or other pharmacokinetic parameters, among patients is reduced), resulting in fewer "non-responders" to the treatment. In addition, administration of colchicine as sustained release is resistant to dose dumping, therefore the dissolution of the composition is not significantly influenced by alcohol.

Further, sustaining the release expands the time where colchicine is present in the blood in therapeutic levels. This results in a more efficient inhibition of disease progression and, thus, improving the clinical outcome.

Furthermore, for the prophylactic uses described herein, colchicine does not have to go deep into the tissue (like for gout), it may be active in the blood system directly (in the vessels) where it acts on the plaques and especially on inflammatory blood cells (neutrophils). This means, less total colchicine and lower serum levels can be therapeutic. Fast and high colchicine levels, e.g., as for treating an acute gout flare can be avoided. Thus, lower levels of colchicine, e.g., about 0.1 to about 0.75 mg sustained release formulations as described above (or even less frequent doses), may be sufficient to achieve the desired clinical outcome.

In the normal situation, most colchicine is absorbed from the small intestine and most passes the liver (some is also excreted in the urine via kidney). There it is metabolized but quite a large proportion of colchicine goes through the liver un-metabolized. This means, it goes through the liver into the bile and from there it is excreted into the big intestine (colon). There it can be resorbed into the body again which leads to the characteristic second peak (accounts for about 50% of totally absorbed colchicine and is thought to be responsible for gastrointestinal problems, such as diarrhea). If colchicine is formulated as a sustained release preparation as described above, a slower release of colchicine results in a slower resorption. This results in more complete metabolism of colchicine in the liver (because it is less busy with colchicine at a time) and, thus, less recirculation of un-metabolized colchicine. This consequently reduces the incidence of gastrointestinal problems and increases compliance. Colchicine administered as sustained release in accordance with the present invention may also be beneficial for other known side/adverse effects associated with colchicine treatment/administration (the skilled person is well aware of the adverse effects that may occur upon colchicine administration or colchicine treatment). Thus, administration of colchicine as sustained release, as described above, results in a safety increase and safety benefit.

IV. Methods of Preparing a Sustained Release Formulation

The current invention additionally encompasses a method of preparing formulations of colchicine, comprising a sustained release component, and an optional immediate release component, wherein colchicine is released from the formulation at the sustained rate along the pre-determined or desired release profile.

In one embodiment, the colchicine compositions described in the present invention is in the form of a tablet. As used herein, the term "tablet" means a compressed pharmaceutical dosage form of any shape or size. The tablets described herein may be obtained from the compositions comprising colchicine and a pharmaceutically acceptable excipient. Any of the colchicine compositions can be in the form of any other dosage form known in the art, specifically, any oral dosage form, for example a capsule.

In a first aspect of the invention, there is provided a controlled release formulation for use in oral dosage forms. The formulation includes a mixture containing hypromellose as a hydrophilic matrix, which is effective to provide controlled release of a pharmaceutically active ingredient.

Matrix systems are well known in the art. In a typical matrix system, the drug is homogenously dispersed in a polymer in association with conventional excipients. This admixture is typically compressed under pressure to produce a tablet. The API is released from the tablet by diffusion and erosion. Matrix systems are described in detail by (i) Handbook of Pharmaceutical Controlled Release Technology, Ed. D. L. Wise, Marcel Dekker, Inc. New York, N.Y. (2000), and (ii) Treatise on Controlled Drug Delivery, Fundamentals, Optimization, Applications, Ed. A. Kydonieus, Marcel Dekker, Inc. New York, N.Y. (1992), the contents of both of which are hereby incorporated by reference.

When the tablet is exposed to aqueous media, such as in the gastrointestinal tract, the tablet surface wets and the polymer begins to partially hydrate forming an outer gel layer. This outer gel layer becomes fully hydrated and begins to erode into the aqueous fluids. Water continues to permeate toward the core of the tablet permitting another gel layer to form beneath the dissolving outer gel layer. These successive concentric gel layers sustain uniform release of the API by diffusion from the gel layer and exposure through tablet erosion. In the case of the mixtures of the present invention, when included in a compressed tablet matrix, the hypromellose provides a hydrophilic swellable structure capable of functioning as the gel layer. In this way, the drug release is controlled.

In accordance with one embodiment, the colchicine formulation of the present invention can be manufactured by either wet or dry granulation of a colchicine composition, blending the resulting granulate with excipients, and then compressing the composition into tablets.

In one embodiment, wet granulation is used to prepare wet granules comprising colchicine. A granulating liquid is used in wet granulation process. Both aqueous and non-aqueous liquids may be used as the granulating liquid. In one embodiment, the granulating liquid is an aqueous liquid, or more specifically, purified or de-ionized water. The amount of the granulating liquid used may depend on many factors, for example, the type of the granulating liquid, the amount of the granulating liquid used, the type of excipient used, the nature of the active agent, and the active agent loading.

In one embodiment, the colchicine particles and suitable excipients are mixed with the granulating liquid for a sufficiently long period to facilitate good distribution of all starting materials and good content uniformity. Wet granulation is generally performed at temperatures between about 20° C. to about 35° C., or more specifically, at room temperature (about 25° C.). Following wet granulation, the granulate is dried at increased temperatures to yield a dry granulate. In an embodiment, the step of drying may be performed for a sufficiently long period until the desired residual moisture content is reached. In an embodiment, this may be about 45° C. for about 12-48 hours. It should be appreciated that the overall time to perform the granulation process may depend on a variety of factors, including but not limited to, the solvents used, batch size, instruments used, etc.

Any equipment may be used to contact the granulating liquid with the colchicine and the excipients as long as uniform distribution of the granulating liquid is achieved. For example, small-scale production can be achieved by mixing and wetting the colchicine and the excipients in mortars or stainless steel bowls, while for larger quantities, V-blenders with intensifier bars, planetary mixers, rotary granulators, high shear granulators, and fluid-bed granulation equipment may be used. In one embodiment, the granulator is a high shear granulator.

In one embodiment, a method of making a colchicine composition comprises wet granulating colchicine with pharmaceutically acceptable excipients and a granulating liquid to obtain wet granules, and mixing the granules in a next step with a second excipient to obtain a colchicine composition. In one embodiment, the pharmaceutically acceptable excipient comprises a binder and a filler. In an embodiment, the binder may be Hypromellose. In an embodiment, the filler may be lactose monohydrate and pregelatinized starch. In another embodiment, purified water is used as the granulating liquid. In an embodiment, the second excipient mixed with the granules may be a filler. In an embodiment, the filler may be lactose monohydrate. The colchicine compositions can contain about 0.1 wt % to about 10 wt %, or more specifically, about 0.25 wt % to about 0.75 wt %, of colchicine, based on the total weight of the colchicine composition.

In an embodiment, the method of making a composition comprises wet granulating colchicine with a pharmaceutically acceptable excipient to obtain wet granules, and mixing the granules with a filler to obtain a colchicine composition. In some embodiments, the method further includes drying the mixture. In another embodiment, the wet granules are dried to obtain dried granules, and then the dried granules are mixed with a binder, a filler, or both to obtain the composition. In another embodiment, the dried granules can be milled to obtain milled granules before mixing the milled dried granules with the binder, a filler, or both. The method can further include mixing the colchicine composition with a glidant, a lubricant, or both to obtain a blend or compressing the blend to obtain a tablet. In one embodiment, the glidant may be Talc. In another embodiment, the lubricant may be Stearic acid. The method can further include coating the tablet.

In another embodiment, a method of making a colchicine tablet comprises wet granulating colchicine with a pharmaceutically acceptable excipient to obtain wet granules; drying the wet granules to obtain dried granules; milling the dried granules to obtain milled granules; mixing the milled granules with a filler to obtain the composition; mixing the composition with a glidant, a lubricant, or both to obtain a blend; and compressing the blend to obtain a colchicine tablet of the present invention.

In some embodiments, the wet granules are dried to obtain dried granules before mixing with a second excipient, for example a filler. Wet granules can be dried by any suitable means to remove the granulating liquid and to form dried granules containing colchicine and the pharmaceutically acceptable excipient. The conditions and duration of drying depend on factors such as the liquid used and the weight of the granulating particles. Examples of suitable drying methods include, but are not limited to, tray drying, forced air drying, microwave drying, vacuum drying and fluid bed drying.

After drying, dried granules may be mixed directly with an excipient, for example, a filler, a binder, or a lubricant, for further processing. Alternatively, dried granules may optionally be subjected to additional processing steps prior to mixing with the excipient. For example, dried granules may be sized to reduce particle size prior to mixing with an excipient. Exemplary sizing operations include milling or sieving. Any suitable equipment for reducing the particle size may be used in the present invention.

Suitable excipients may be added extragranularly and mixed with the granules to form colchicine compositions. As used herein, the term "extragranular" or "extragranularly" means that the referenced material, for example, a suitable excipient, is added or has been added as a dry component after wet granulation. In one embodiment, a filler, a binder, a glidant and a lubricant are added extragranularly to the granules and mixed to form a blend. The blend may be encapsulated directly into capsule shells, for example, hard gelatin shells, to form capsule formulations. Alternatively, the blend may be compressed into tablets. In some embodiments, the granules are dried granules or milled, dried granules.

Mixing can be carried out for a sufficient time to produce homogeneous mixtures or blends. Mixing may be accomplished by blending, stirring, shaking, tumbling, rolling, or by any other method to achieve a homogeneous blend. In some embodiments, the components to be mixed are combined under low shear conditions in a suitable apparatus, such as a V-blender, tote blender, double cone blender or any other apparatus capable of functioning under low shear conditions.

The homogenous mixtures or blends are then compressed using any method suitable in the industry. The mechanical force will define the physical properties of the tablets, especially the crushing strength of the resulting tablet. The mechanical strength interacts with the initial swelling of the tablet and dilution speed of the tablet core. This effect is well known in the art and can be adjusted and controlled during the lifecycle of the product. For the colchicine sustained-release formulation of the present invention, the compression strengths used may range from about 30N to about 130N. In one embodiment, the compression strength may be about 100N. In another embodiment, the compression strength may be about 100N+/-15N.

The colchicine tablets prepared from the above described methods exhibit acceptable physical characteristics including good friability and hardness. As per EP and USP guidelines, the colchicine tablets disclosed herein have friability in the range of about 0% to less than about 1%.

The colchicine tablet can be coated. Coating the tablet may be performed by any known process. A coating for the colchicine tablet disclosed herein can be any suitable coating, such as, for example, a functional or a non-functional coating, or multiple functional or non-functional coatings. By "functional coating" is meant to include a coating that modifies the release properties of the total formulation, for example, a sustained-release coating. By "non-functional coating" is meant to include a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition.

In one embodiment, a colchicine composition comprises colchicine, a binder, a filler, a retarding agent, a glidant, and a lubricant. In an embodiment, a colchicine composition comprises about 0.25 to about 0.75 mg colchicine; about 10 to about 80 mg lactose monohydrate; about 5 to about 50 mg pregelatinized starch; about 1 to about 30 mg Hypromellose 6 mPa*s; about 5 to about 40 mg Retalac (compound of lactose monohydrate and Hypromellose 4000 mPa*s 50/50 w/w %); about 0.5 to about 5 mg Talc; and about 0.5 to about 5 mg Stearic acid 50. In an embodiment, the colchicine composition comprises about 0.5 mg colchicine, about 59 mg lactose monohydrate; about 7.5 mg pregelatinized starch; about 1 mg Hypromellose 6 mPa*s; about 30 mg Retalac (compound of lactose monohydrate and Hypromellose 4000 mPa*s 50/50 w/w %); about 1 mg Talc; and about 1 mg Stearic acid 50. The colchicine dosage form has a total weight of about 100 mg. The colchicine composition can be in the form of a tablet.

V. Treatment Methods Using Sustained Release Colchicine

The present invention also presents a method of treatment or prevention of cardiovascular diseases and/or inflammatory disorders in a subject, comprising administering to the subject a therapeutically effective amount of a colchicine formulation of the present invention, wherein colchicine is released from the formulation at a sustained rate along a pre-determined or desired release profile. The method of the current invention possesses the flexibility to selectively adjust the pharmacokinetics of the administered formulations depending on the nature of the condition and needs of the patients due to the novel design of the colchicine formulation that comprises an extended release component and an optional immediate release component, and the release profiles of both components can be selectively modified during the preparation process as described above to comply with the predetermined release profile.

In one embodiment, treatment includes the application or administration of a colchicine formulation as described herein to a patient, where the patient has, or has the risk of developing a cardiovascular disease and/or an inflammatory disorder. In another embodiment, treatment is also intended to include the application or administration of a pharmaceutical composition comprising the colchicine formulation, to a patient, where the patient has, or has the risk of developing a cardiovascular disease and/or inflammatory disorder.

As used herein, the term "cardiovascular disease" refers to any disease involving the heart and/or the vascular system (all blood vessels incl. arteries, capillaries and veins). This includes all diseases listed in chapter IX "Diseases of the circulatory system (I00-I99)" of the International Statistical Classification of Diseases and Related Health Problems 10th Revision (ICD-10) Version for 2010, by the World Health Organisation.

More specifically, all diseases of this ICD-10 class which involve a) inflammation of any part of the heart or blood vessel as well as b) ischemia/atherosclerosis/thickening of any blood vessel of the circulatory system.

Colchicine as described herein is for use in the treatment and/or prevention of any inflammatory disorder involving the heart tissue selected from ICD-10 sections I00-I99. More specifically, these include acute and recurrent pericarditis as well as post-surgical complications involving inflammation of the pericardium (Postcardiotomy syndrome, Postpericardiotomy syndrome, pericardial effusion). Other inflammatory heart diseases covered are any form of myocarditis, endocarditis and arterial fibrillation.

The proposed mechanism of action in this indication is the inhibition of plaque instability by neutrophil inhibition. In stable coronary disease, fatty materials accumulate at the blood vessel and form a stable plaque. This plaque may become subject to attack by neutrophils. This may cause plaque instability and consequently leads to plaque rupture and clinical events. Therefore, colchicine as described herein is for use in treatment and/or prevention of any disease of the cardiovascular system which involves ischemia, atherosclerosis and/or thickening of blood vessels (arteries, capillaries, veins) due to plaque formation with a risk of clinical events due to plaque instability. Claimed are all diseases classified in ICD-10 section I00-I99 fulfilling any of these requirements. Examples are stable coronary disease, cardiovascular atherosclerosis, and atherosclerosis of the peripheral vascular system, Abdominal Aortic Aneurysm (AAA) and carotid and iliofemoral/renal atheromas (e.g. I25, I70).

In the context of the present invention, an acute cardiovascular event in a patient with stable cardiovascular disease is preferably a cardiovascular event in a patient with stable coronary disease. In the context of the present invention, the term "stable coronary disease" and "stable coronary heart disease" have the same meaning and are used interchangeable. Both terms include the medical condition stable coronary artery disease (SCAD). "Stable" in the context of the terms "stable cardiovascular disease", "stable coronary disease" or "stable coronary heart disease" is defined as any conditions of diagnosed cardiovascular disease in the absence of acute cardiovascular events. Hence, e.g. stable coronary disease defines the different evolutionary phases of coronary disease, excluding the situations in, which coronary artery thrombosis dominates clinical presentation (acute coronary syndrome).

Colchicine in the context of the present invention can be used for the prevention and/or treatment of cardiovascular diseases. Cardiovascular diseases include, but are not limited to, heart diseases as described, e.g., in Robbins and Cotran, Pathologic Basis of Disease, Eighth Edition, Saunders Elsevier. Cardiovascular disease refers to a group of diseases of the circulatory system including the heart, blood and lymphatic vessels. In particular, cardiovascular disease may include vascular diseases involving atherosclerosis, plaque formation or disposition. The most common cardiovascular diseases are coronary heart disease and stroke. Non-limiting examples of cardiovascular disease which may be prevented or treated according to the methods of the invention include coronary heart disease (disease of the blood vessels supplying the heart muscle), cerebrovascular disease (disease of the blood vessels supplying the brain), peripheral arterial disease (disease of blood vessels supplying the arms and legs), rheumatic heart disease (damage to the heart muscle and heart valves from rheumatic fever, caused by streptococcal bacteria), congenital heart disease (malformations of heart structure existing at birth), deep vein thrombosis and pulmonary embolism (blood clots in the leg veins, which can dislodge and move to the heart and lungs), hyperlipemia (an excessive level of blood fats, such as LDL), high blood pressure, coronary artery disease, atherosclerosis, ischemic diseases, abdominal aortic aneurism, carotid and iliofemoral/renal atheromas, heart failure, cardiac rhythm defects, arteriosclerosis, heart attack and stroke. Heart attacks and strokes are usually acute events and are mainly caused by a blockage that prevents blood from flowing to the heart or brain. The most common reason for this is a build-up of fatty deposits on the inner walls of the blood vessels that supply the heart or brain. Strokes can also be caused by bleeding from a blood vessel in the brain or from blood clots.

Especially, in the context of the present invention, colchicine can be used for the prevention of acute pericarditis, recurrent pericarditis, recurrent pericarditis in patients with a history of pericarditis, post-pericardiotomy syndrome (PPS), PPS in patients undergoing cardiac surgery, and cardiovascular events in patients with stable coronary (heart) disease (the cardiovascular events can be acute cardiovascular events). In some embodiments, colchicine according to the present invention is not used to treat acute pericarditis. In other embodiments, colchicine according to the present invention is not used to treat recurrent pericarditis.

Pericarditis is an inflammatory disease involving the pericardium, a thin double-walled fibroelastic sac, surrounding the heart. Due to inflammation, it comes to irritation and swelling of the pericardium. This causes the sac to rub against the heart which causes chest pain, the most common symptom of pericarditis. Pericarditis is the most common form if inflammatory disorder of the heart, though very rare on a population basis. Pericarditis is very heterogeneous in its origin, clinical manifestations and duration of symptoms. It can either occur as isolated clinical problem or as a manifestation of a systemic disease. In most cases (90%), pericarditis is of idiopathic (spontaneous, unknown) etiology but may also occur secondary to systemic infections, acute myocardial infarction or autoimmune diseases. The post-pericardiotomy syndrome (PPS) may be a troublesome complication following cardiac surgery occurring a few days to several weeks after the surgical operation. The estimated incidence of the syndrome has a relatively wide range affecting from 10 to 40% of patients submitted to cardiac surgery (Prince and Cunhe, 1997, Heart Lung, 26:165).

Non-limiting examples of (acute) cardiovascular events are injury of the atherosclerotic wall, acute coronary syndrome, out-of-hospital cardiac arrest, or noncardioembolic ischemic stroke. Further such events are described, e.g., in Robbins and Cotran, Pathologic Basis of Disease, Eighth Edition, Saunders Elsevier.

In an embodiment, the colchicine formulation of the present invention may be used to treat inflammatory disease other than those mentioned above. In an embodiment, the inflammatory disease includes, but is not limited to, gout, familial Mediterranean fever, Behcet's disease, Age-related macular degeneration and Alzheimer's disease.

Patients/subjects which suffer from the above described disease and/or which are suitable for treatment with colchicine according to the present invention can be diagnosed by conventional and/or routine procedures. The skilled person is well aware of them. Diagnosis is also described, e.g., in Robbins and Cotran, Pathologic Basis of Disease, Eighth Edition, Saunders Elsevier.

In an embodiment, the colchicine formulation as described herein is useful for the treatment of various cardiovascular diseases and/or inflammatory disorders. In some embodiments, treatment of a cardiovascular disease and/or an inflammatory disorder is intended to include remediation of, improvement of, amelioration of, lessening of the severity of, or reduction in the time course of, a disease, disorder or condition, or any parameter or symptom thereof. In an embodiment of the present invention, the term "disorder", "disease", or "condition" is to be understood as cardiovascular disease and/or inflammatory disorder as described above. In the context of the present invention, "amelioration" refers, without limitation, to any observable beneficial effect.

In accordance with the present invention, the colchicine formulation herein can be used to promote a positive therapeutic response with respect to the cardiovascular disease and/or inflammatory disorder. A "positive therapeutic response" with respect to the cardiovascular disease and/or inflammatory disorder is intended to include an improvement in the disease can be evidenced by, for example, a delayed onset of clinical symptoms of the disease or condition, a reduction in severity of some or all clinical symptoms of the disease or condition, a slower progression of the disease or condition, an improvement in the overall health or well-being of the subject, or by other parameters well known in the art that are specific to the particular disease.

In another embodiment, the colchicine formulation as described herein is useful in the prevention of various cardiovascular diseases and/or inflammatory disorders. In the context of the present invention, the term "prevention" is well known in the art. For example, a patient/subject suspected of being prone to suffer from a disorder or disease as defined herein may, in particular, benefit from a prevention of the disorder or disease. The subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician. Prevention includes, without limitation, to avoid the disease or condition from occurring in patient and/or subject that may be predisposed to the disease but does not yet experience or exhibit symptoms of the disease (prophylactic treatment).

Colchicine according to the present invention may also be used in combination with conventional therapy for any of the diseases disclosed herein. Such conventional therapies are well known in the art and the skilled person knows any such therapies. Colchicine as described herein may also be used in combination with colchicine-compatible statins. In general, non-limiting examples of statins are atorvastatin (Lipitor®, Torvast®), fluvastatin (Lescol®), lovastatin (Mevacor®, Altocor®, Altoprev®), pitavastatin (Livalo®, Pitava®), pravastatin (Pravachol®, Selektine®, Lipostat®), rosuvastatin (Crestor®) and simvastatin (Zocor®, Lipex®). In connection with the present invention, colchicine-compatible statins are used. Preferably, in the context of the present invention, the combination of the composition of the present invention with the colchicine-compatible statins are accomplished in connection with stable coronary heart disease. Such statins preferably are statins which, due to the nature of their mechanism of action, metabolism and/or clearance do not, or only to a small extent, interfere with the mechanism of action, metabolism and/or clearance of colchicine and therefore show a reduced risk, severity and/or incidence of drug-related drug adverse events when given in combination with colchicine.

In an embodiment, the use of colchicine is in fixed (within the same pharmaceutical preparation) or unfixed (different pharmaceutical preparation) combination. "Fixed combination" is to be understood as meaning a combination whose active ingredients are combined at fixed doses in the same vehicle (single formula) that delivers them together to the point of application. Fixed combination can mean, e.g., in a single tablet, solution, cream, capsule, gel, ointment, salve, patch, suppository or transdermal delivery system. "Unfixed combination" as used herein is to be understood as meaning that the active ingredients/components are in more than one vehicle (e.g. tablets, solutions, creams, capsules, gels, ointments, salves, patches, suppositories or transdermal delivery systems). Each of the vehicles can contain a desired pharmaceutical composition or active component. For example, a preferred unfixed combination as described herein means that one vehicle contains colchicine, as described herein, and another vehicle contains a colchicine-compatible statin, as described herein. Examples of colchicine as described herein in fixed or unfixed combination(s) encompass(es) colchicine in combination with one or more colchicine-compatible statins selected from the group consisting of atorvastatin, rosuvastatin, simvastatin and pravastatin. Specifically, colchicine as described herein in fixed or unfixed combination is to be understood as meaning colchicine in combination with atorvastatin. Specifically, colchicine as described herein in fixed or unfixed combination is to be understood as meaning colchicine in combination with rosuvastatin. Specifically, colchicine as described herein in fixed or unfixed combination is to be understood as meaning colchicine in combination with simvastatin. Specifically, colchicine as described herein in fixed or unfixed combination is to be understood as meaning colchicine in combination with pravastatin.

In some embodiments, colchicine as described herein may be used in combination with a statin and another agent, such as ezetimibe/simvastatin. Colchicine as described herein may be used in combination with other drugs, e.g, which are used in medicine and are known to the skilled person (e.g. antibiotics, NSAID (non-steroidal anti-inflammatory drugs), corticosteroids).

VI. Administration Methods

Methods of preparing and administering the colchicine formulation of the present invention to a subject in need thereof are well known to or are readily determined by those skilled in the art. The route of administration of the colchicine formulation can be, for example, oral, parenteral, by inhalation or topical. The term parenteral as used herein includes, e.g., intravenous, intraarterial, intraperitoneal, intramuscular, subcutaneous, rectal, or vaginal administration.

Colchicine when used as a composition in the context of the present invention may include one or more pharmaceutically acceptable carriers and thus may be prepared in the form of a local formulation, in order for it to be administered. The pharmaceutically acceptable carrier may include saline, sterile water, linger liquid, buffer saline, a dextrose solution, a malto dextrin solution, glycerol, ethanol and mixtures of one or more thereof, and also may include an additive such as an antioxidant, a buffer, a bacteriostatic agent or the like, as necessary. Furthermore, a diluent, a dispersant, a surfactant, a binder and a lubricant may be added when the composition according to the present invention is prepared, e.g., in the form of a local formulation such as an ointment, lotion, cream, gel, skin emulsion, skin suspension, patch or spray.

Non-limiting examples for administration of the compound and or compositions according to the present invention include coated and uncoated tablets, soft gelatine capsules, hard gelatine capsules, lozenges, troches, solutions, emulsions, suspensions, syrups, elixiers, powders and granules for reconstitution, dispersible powders and granules, medicated gums, chewing tablets and effervescent tablets. The composition according to the present invention can administered in any pharmaceutical form for oral (e.g. solid, semi-solid, liquid), dermal (e.g. dermal patch), sublingual, parenteral (e.g. injection), ophthalmic (e.g. eye drops, gel or ointment) or rectal (e.g. suppository) administration. In an embodiment, the composition is formulated as a tablet, capsule, suppository, dermal patch or sublingual formulation.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Certain pharmaceutical compositions used in this invention can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of the colchicine formulation to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

In some situations, the composition of the present invention can be parenterally administered. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01-0.1 M and preferably 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

Parenteral formulations can be a single bolus dose, an infusion or a loading bolus dose followed with a maintenance dose. These compositions can be administered at specific fixed or variable intervals, e.g., once a day, or on an "as needed" basis.

The composition according to the present invention may be administered in a dose range varying depending on the patient's body weight, age, gender, health condition, diet, administration time, administration method, excretion rate and disease severity. The compounds of the present invention as compounds per se in their use as pharmacophores or as pharmaceutical compositions can be administered to the patient and/or subject at a suitable dose. The dosage regiment will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition comprising the herein defined should be, e.g., in a range as described below. Progress can be monitored by periodic assessment.

The composition according to the present invention can be administered with a single dose or with 2, 3, 4, 5, 6, 7, 8, 9, or 10 doses, if desired. The composition can be administered 1, 2, 3, 4, 5, 6, 7, 8, 9 or 10 times per day. Preferably, colchicine according to the present invention is administered once per day. More preferably, colchicine according to the present invention is administered once per day as a single dose.

The composition according to the present invention can be administered regularly for long periods of time. In an embodiment, the composition can be administered regularly for 1, 2, 3, 4, 5, 6, 7, 8, 9, 10 or more years. In another embodiment, the composition can be administered regularly for 1, 2, 3, 4, 5, 6, 7, 8, 9, 10, 11, 12 or more months. In other embodiments, the composition can be administered regularly for 1, 2, 3, 4, 5, 6, 7, 8, 9, 10 or more weeks. As used herein, the term "regularly" refers to administration of the composition at regular times or intervals over a period of time. For instance, the composition may be administered to a patient once daily for three years. In other embodiments, the composition may be administered to a patient once every other day for 5 years. It should be appreciated that the frequency of administration may vary based on a number of factors, including, but not limited to, the severity of disease, the overall health of the patient, any additional medications the patient is taking, and whether the treatment is prophylactic or not. It should also be appreciated that the frequency of administration may be adjusted at any point.

The amount/concentration/dose of the composition according to the present invention can be between 0.1 mg and 5.0 mg, 0.1 mg and 2.0 mg, 0.1 mg to 1.5 mg, 0.1 mg to 1.0 mg, 0.1 mg to 0.75 mg, 0.1 mg to 0.5 mg, 0.25 mg to 5.0 mg, 0.25 mg to 2.0 mg, 0.25 mg to 1.5 mg, 0.25 mg to 1.0 mg, 0.25 mg to 0.75 mg or 0.25 mg to 0.5 mg. In an embodiment, the composition according to the present invention is administered at a daily dose of colchicine of between about 0.1 mg and about 0.75 mg or between about 0.1 mg and about 0.5 mg. In another embodiment, the composition according to the present invention is administered at a daily dose of colchicine of between about 0.25 mg to about 0.75 mg or between about 0.25 mg to about 0.5 mg. In an embodiment, the composition according to the present invention is administered at a daily dose of about 0.5 mg colchicine.

In a preferred embodiment, the amount/concentration of colchicine as used herein can be administered at the first day of administration in a higher dose (concentration/amount) compared to the administration of colchicine at the following days(s) of administration (maintenance administration/maintenance dose of administration). Alternatively such decreased dose (maintenance dose) can be started after 2, 3, 4, 5, 6, 7, 8, 9 or 10 days of initial administration of the higher dose. In case the course of treatment is any such as described above, the higher dose/amount/concentration of colchicine (e.g. at the first day of administration) can be any as described above, provided that the maintenance dose (the dose/amount/concentration of colchicine at the days following the higher dose/amount/concentration) is lower than the initial dose/amount/concentration of colchicine (e.g. at the first day of administration). Preferably, the composition of the invention is administered with a dose of colchicine of between about 1.0 mg to about 2.0 mg at the first day (preferably as a single dose) of administration and the maintenance dose of colchicine at the following day(s) of administration is between about 0.5 mg to about 1.0 mg.

In keeping with the scope of the present disclosure, the colchicine formulation of the present invention can be administered to a human or other animal in accordance with the aforementioned methods of treatment in an amount sufficient to produce a therapeutic effect. The colchicine formulation can be administered to such human or other animal in a conventional dosage form prepared by combining the colchicine formulation of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

By "therapeutically effective dose or amount" or "effective amount" is intended an amount of the colchicine formulation that when administered brings about a positive therapeutic response with respect to treatment of a patient with a disease to be treated, e.g., an improvement in the disease can be evidenced by, for example, a delayed onset of clinical symptoms of the disease or condition, a reduction in severity of some or all clinical symptoms of the disease or condition, a slower progression of the disease or condition, an improvement in the overall health or well-being of the subject, or by other parameters well known in the art that are specific to the particular disease.

The invention also provides for the use of the colchicine formulation in the manufacture of a medicament for treating a subject for treating a cardiovascular disease and/or inflammatory disorder, wherein the medicament is used in a subject that has been pretreated or is concurrently being treated with at least one other therapy. By "pretreated" or "pretreatment" is intended the subject has received one or more other therapies prior to receiving the medicament comprising the colchicine formulation. "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the colchicine formulation. By "concurrent" or "concomitant" is intended the subject is receiving one or more other therapies while at the same time receiving the medicament comprising the colchicine formulation. It is not necessary that the subject was a responder to pretreatment with the prior therapy or therapies or a responder to the concurrent therapy or therapies. Thus, the subject that receives the medicament comprising the colchicine formulation could have responded, or could have failed to respond, to pretreatment with the prior therapy, or to one or more of the prior therapies where pretreatment comprised multiple therapies.

All of the references cited above, as well as all references cited herein, are incorporated herein by reference in their entireties.

While the invention has been illustrated and described in detail in above, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The present invention is additionally described by way of the following illustrative non-limiting examples that provide a better understanding of the present invention and of its many advantages. The following examples are included to demonstrate preferred embodiments of the invention. It should be appreciated by those of skill in the art that the techniques disclosed in the examples which follow represent techniques used in the present invention to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1: Colchicine Sustained Release Tablet

This example illustrates a colchicine sustained release tablet. The tablet uses the ingredients and concentrations shown in Table 1 below.

| Ingredient | mg/Tablet | Tablet % | Function |
|---|---|---|---|
| Colchicine | 0.500 | 0.5 | Active Pharmaceutical Ingredient (API) |
| Lactose monohydrate | 59.00 | 59.0 | Filling Agent |
| Pregelatinized Starch | 7.50 | 7.5 | Filling Agent |
| Hypromellose 6 mPa * s | 1.000 | 1.0 | Binder |
| Purified water[1] | q.s. | q.s. | Diluent for API and Binder |
| Lactose monohydrate | 10.00 | 10.00 | Filling Agent |
| Retalac (Compound of Lactose monohydrate and Hypromellose 4000 mPa * s 50/50 w/w %) | 20.00 | 20.00 | Retarding Agent |
| Talc | 1.00 | 1.0 | Glidant |
| Stearic acid 50 | 1.00 | 1.0 | Lubricant |
| Total tablet weight [mg] | 100.00 | | [1]removed within the process |

The concentrations may be altered to change certain properties of the formulations, for instance, the dissolution profile. Table 2 shows the ranges for each ingredient.

| Ingredient | Range | Function |
|---|---|---|
| Colchicine | 0.5-0.75 | Active Pharmaceutical Ingredient (API) |
| Lactose monohydrate | 10-80 | Filling Agent |
| Pregelatinized Starch | 5-50 | Filling Agent |
| Hypromellose 6 mPa * s | 1-30 | Binder |
| Purified water[1] | q.s. | Diluent for API and Binder |
| Lactose monohydrate | 10-30 | Filling Agent |
| Retalac (Compound of Lactose monohydrate and Hypromellose 4000 mPa * s 50/50 w/w %) | 5-40 | Retarding Agent |
| Talc | 0.5-5 | Glidant |
| Stearic acid 50 | 0.5-5 | Lubricant |
| Total tablet weight [mg]: | | [1]removed within the process |

Example 2: Method of Making a Colchicine Sustained Release Tablet

The above ingredients are utilized to make a tablet to the following working directions:

Granulation:

The granulation was performed in a Kenwood mixer. The colchicine and hypromellose 6 Mpa*s were first weighed and separately dissolved into purified water. This solution of hypromellose 6 Mpa*s was filled in the mixer containing the lactose within 1.5 min followed by a 3 minute mixing time. Subsequently, the dissolved colchicine was sprayed with a filing agent (e.g., lactose monohydrate) under continuous mixing over a period of 15 minutes. These steps were performed at room temperature. The wet granulate was then passed through a 1.0 mm hand sieve. It was then dried in an oven (Haeraeus™) at 45° C. for 26 h to a residual moisture content of 0.53%, and passed through a 0.8 mm sieve shaker (Erweka AR 400). Density parameters were tested (Engelmann). Bulk density 0.53 g/ml, compacted bulk density 0.67 g/ml, Hausner ratio 1.26. Rheology:Flow time 4 sec; Slope angle 23.8°.

Blending:

Following the granulation process, the granulate is compounded with a filling agent (e.g., lactose monohydrate), a retarding agent (e.g., Retalac), and other excipients (e.g., flow enhancer, glidants and/or lubricants) to support the tablet compression process. To this end, these ingredients were placed manually through a 0.8 mm sieve and mixed with the granulate in a cube mixer (Erweka) for 10 minutes. In one embodiment, the glidant used may be Talc. In another embodiment, the lubricants used may be Stearic acid. The granulate will then be blended using a suitable mixer.

Compression of Tablets:

To form the tablets, a compression force is needed. The mechanical force will define the physical properties of the tablets, especially the crushing strength of the resulting tablet. The mechanical strength interacts with the initial swelling of the tablet and dilution speed of the tablet core. This effect is well known in the art and can be adjusted and controlled during the lifecycle of the product.

Tableting was performed on a Korsch (EK 0) tablet press with a round tabletting tool, biconvex, 6 mm in diameter. Average tablet hardness was approximately 100N+/−15 N. Tablets measured about 100 mg in mass, friability was not measurable. Breaking strength and hardness were measured with a Erweka Multickeck. Friability was measured with a Erweka Friabilator and a Mettler analytical balance. The dimensions were measured using a Mitutoyo caliper.

Example 3: Measurements of Dissolution Profiles of Sustained-Release Colchicine Formulations The dissolution of the sustained release formulation of colchicine was measured at various time points. The compositions were dissolved in 500 ml of water at 37° C. and stirred continuously over a period of 6 hours. Samples were drawn at several time points to study the kinetics of the dissolution process of the drug substance within the hydrophilic matrix system. Colchicine content in the samples was analyzed using HPLC analysis.

Several batches were tested to determine the optimal dissolution profile for the sustained release formulation. The release can be modified by both the concentration of hypromellose or by using different viscosity grades of hypromellose (e.g. 1000 mPa or 10000 mPa). In the batches tested below, the viscosity grade remained constant, however, the concentration of hypromellose 4000 mPa in the tablet was modified.

Table 3 below summarizes the various compositions that were tested.

| Material name | Mass [%] | Mass per Tbl. [mg] | Per batch [g] | −0.5% | +0.5% |
|---|---|---|---|---|---|
| Stem granulate: (common for 3 Tablet mixings) | | | | | |
| PE Colchicine | 0.500 | 0.500 | 7.50 | 7.46 | 7.54 |
| Lactose monohydrate EP | 59.000 | 59.000 | 885.00 | 880.6 | 889.4 |
| Pregelatinized Starch USP | 7.500 | 7.500 | 112.50 | 111.94 | 113.06 |
| FB Hypromellose 6 mPa * s EP/JP/USP | 1.000 | 1.000 | 15.00 | 14.93 | 15.08 |
| Water purified * for Colchicine | 0.000 | 4.000 | 60.00 | 59.70 | 60.30 |
| Water purified * For Hypromellose | 0.000 | 8.300 | 124.50 | 123.88 | 125.1 |
| Batch 1: Tableting mix 10% Retalac (compression strength = 100N): | | | | | |
| Lactose monohydrate EP (Filling agent ad 100 mg per tablet) | 20.000 | 20.000 | 80.0 | 79.6 | 80.4 |
| PE Retalac (50% Lactose/50% Hypromellose 4000 mPas) | 10.000 | 10.000 | 40.00 | 39.8 | 40.2 |
| Talc EP/JP | 1.000 | 1.000 | 4.00 | 3.98 | 4.02 |
| Stearic acid 50 EP | 1.000 | 1.000 | 4.00 | 3.98 | 4.02 |
| Total tablet weight: | 100.000 | 100.000 | | | |
| Batch 2: Tableting mix 15% Retalac (compression strength = 100N): | | | | | |
| Lactose monohydrate EP (Filling agent ad 100 mg per tablet) | 15.000 | 15.000 | 60.00 | 59.7 | 60.3 |
| PE Retalac (50% Lactose/50% Hypromellose 4000 mPas) | 15.000 | 15.000 | 60.00 | 59.7 | 60.3 |
| Talc EP/JP | 1.000 | 1.000 | 4.00 | 3.98 | 4.02 |
| Stearic acid 50 EP | 1.000 | 1.000 | 4.00 | 3.98 | 4.02 |
| Total tablet weight: | 100.000 | 100.000 | | | |
| Batch 3: Tableting mix 20% Retalac (compression strength = 100N): | | | | | |
| Lactose monohydrate EP (Filling agent ad 100 mg per tablet) | 10.000 | 10.000 | 40.00 | 79.6 | 80.4 |
| PE Retalac (50% Lactose/50% Hypromellose 4000 mPas) | 20.000 | 20.000 | 80.00 | 79.6 | 80.4 |
| Talc EP/JP | 1.000 | 1.000 | 4.00 | 3.98 | 4.02 |
| Stearic acid 50 EP | 1.000 | 1.000 | 4.00 | 3.98 | 4.02 |
| Total tablet weight: | 100.000 | 100.000 | | | |
| Batch 4: Tableting mix 30% Retalac (compression strength = 50N and 130N): | | | | | |
| Lactose monohydrate EP (Filling agent ad 100 mg per tablet) | 0.000 | 0.000 | 00.00 | 0.0 | 0.0 |
| PE Retalac (50% Lactose/50% Hypromellose 4000 mPas) | 30.000 | 30.000 | 120.00 | 119.40 | 120.60 |
| Talc EP/JP | 1.000 | 1.000 | 4.00 | 3.98 | 4.02 |
| Stearic acid 50 EP | 1.000 | 1.000 | 4.00 | 3.98 | 4.02 |
| Total tablet weight: | 100.000 | 100.000 | | | |
| Batch 5: Tableting mix 0% Retalac (compression strength = 100N): | | | | | |
| Lactose monohydrate EP (Filling agent ad 100 mg per tablet) | 30.000 | 30.000 | 120.00 | 119.40 | 120.60 |
| PE Retalac (50% Lactose/50% Hypromellose 4000 mPas) | 0.000 | 00.000 | 00.00 | 0.0 | 0.0 |
| Talc EP/JP | 1.000 | 1.000 | 4.00 | 3.98 | 4.02 |
| Stearic acid 50 EP | 1.000 | 1.000 | 4.00 | 3.98 | 4.02 |
| Total tablet weight: | 100.000 | 100.000 | | | |

The dissolution profiles of the various batches are provided in Tables 4-6 and FIGS. 1-4. In particular, the dissolution profile for Batches 1-3 is summarized in Table 4 and FIG. 1. The profile for Batch 1 shows approximately a 92% release within about 30 minutes, followed by a constant release. Complete dissolution occurred after 2 hours. Batch 2 shows approximately a 83% release within about 30 minutes, followed by a constant release. Complete dissolution occurred after 2 hours. Batch 3 shows approximately a 74% release within about 30 minutes, followed by a constant release.

TABLE 4

| Concentration Retardant | Sample | Hour 0 | Hour 0.5 | Hour 1 | Hour 2 | Hour 4 |
|---|---|---|---|---|---|---|
| 10% Retalac | 1. | | 90.6 | 98.1 | 99.1 | 98.9 |
| | 2. | | 93.7 | 97.6 | 97.5 | 97.6 |
| | 3. | | 98.6 | 99.3 | 99.5 | 99.8 |
| | 4. | | 93.7 | 97.5 | 98.1 | 98.2 |
| | 5. | | 89.9 | 93.7 | 93.7 | 93.8 |
| | 6. | | 89.6 | 97.2 | 97.5 | 97.6 |
| | Mean | 0 | 92.7 | 97.2 | 97.6 | 97.7 |
| 15% Retalac | 1. | | 75.1 | 89.2 | 95.9 | 96.0 |
| | 2. | | 74.5 | 91.3 | 95.0 | 94.9 |
| | 3. | | 85.7 | 99.1 | 100.3 | 100.2 |

TABLE 4-continued

| Concentration Retardant | Sample | Hour 0 | Hour 0.5 | Hour 1 | Hour 2 | Hour 4 |
|---|---|---|---|---|---|---|
| | 4. | | 86.9 | 98.2 | 100.1 | 99.3 |
| | 5. | | 84.7 | 93.9 | 94.6 | 94.3 |
| | 6. | | 90.7 | 96.0 | 95.7 | 96.1 |
| | Mean | 0 | 82.9 | 94.6 | 96.9 | 96.8 |
| 20% Retalac | 1. | | 68.1 | 87.7 | 97.8 | 97.8 |
| | 2. | | 62.0 | 83.2 | 95.2 | 96.3 |
| | 3. | | 85.4 | 95.2 | 98.2 | 98.3 |
| | 4. | | 76.6 | 94.7 | 97.2 | 96.9 |
| | 5. | | 71.8 | 94.5 | 103.5 | 103.1 |
| | 6. | | 80.6 | 95.4 | 99.0 | 98.9 |
| | Mean | 0 | 74.1 | 91.8 | 98.5 | 98.6 |

Figure 2:
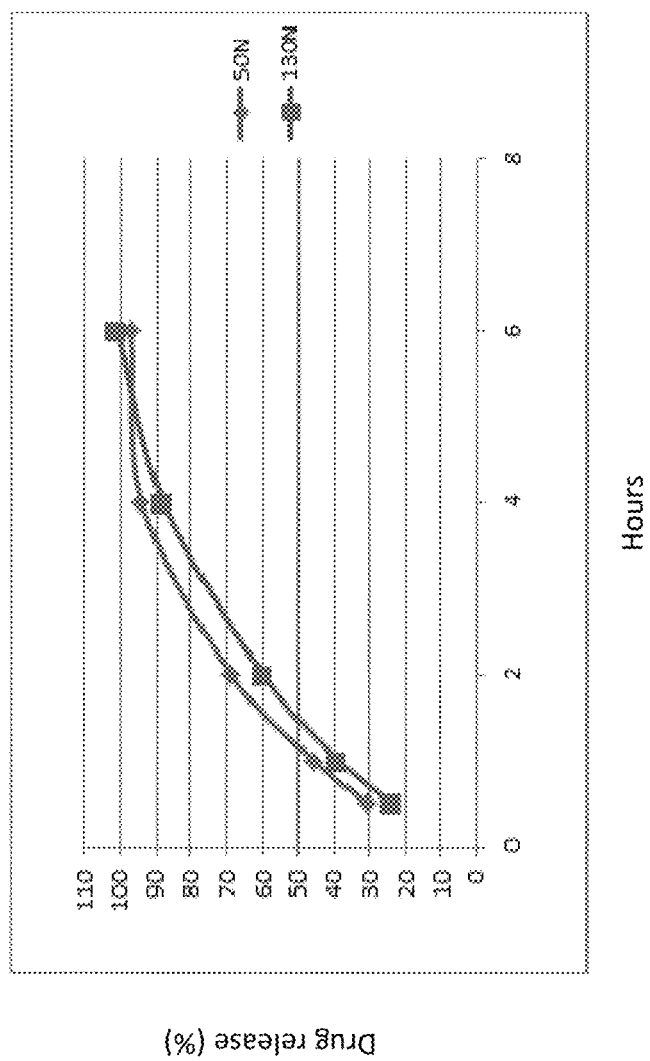
FIG. 2 shows the dissolution profiles for colchicine sustained-release formulation containing 30% of an exemplary retarding agent and tablet hardnesses of 50N and 130N, respectively.
Figure 3:
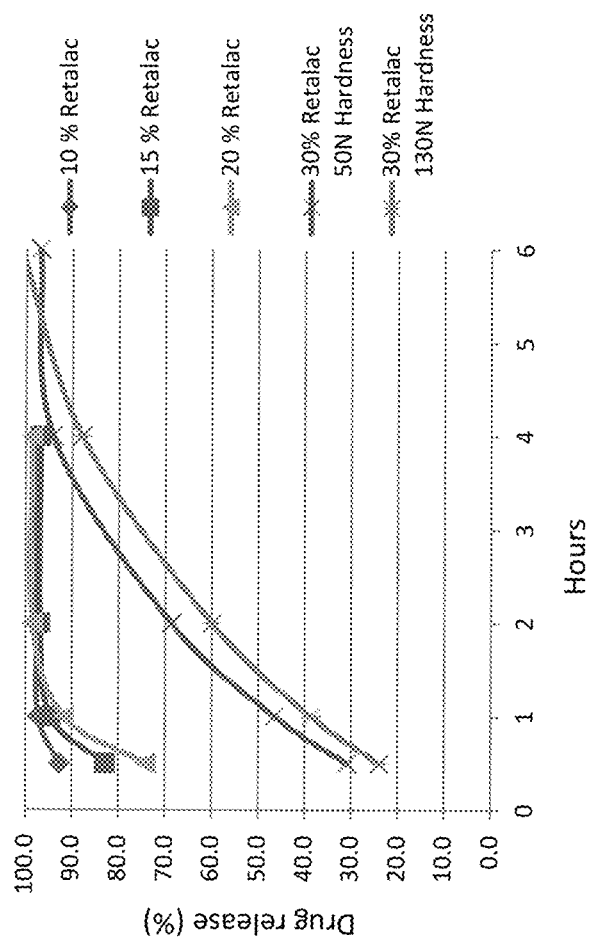
FIG. 3 shows the dissolution profiles for colchicine sustained-release formulations according to FIGS. 1 and 2.

The dissolution profile for Batch 4 is summarized in Table 5 and FIG. 2. Batch 4A shows approximately a 30% release within about 30 minutes, followed by a constant release. Complete dissolution occurred after 6 hours. Batch 4B shows approximately a 23% release within about 30 minutes, followed by a constant release. Complete dissolution occurred within 6 hours. In this example, a difference in tablet hardness results in a difference in release rates. FIG. 3 shows the dissolution profiles for Batches 1-4.

TABLE 5

| Concentration Retardant | Sample | Hour 0.5 | Hour 1 | Hour 2 | Hour 4 | Hour 6 |
|---|---|---|---|---|---|---|
| (A) | No. 1 | 30.5 | 47.1 | 70.7 | 96.5 | 96.9 |
| 30% Retalac | No. 2 | 34.5 | 49.3 | 70.6 | 95 | 98 |
| 50N Hardness | No. 3 | 27.8 | 42.6 | 64.6 | 90.9 | 95.8 |
| | | 30.9 | 46.3 | 68.6 | 94.1 | 96.9 |
| (B) | No. 4 | 22.5 | 37.1 | 54.9 | 81.2 | 92.5 |
| 30% Retalac | No. 5 | 25.9 | 42 | 67.1 | 94.5 | 108.7 |
| 130N Hardness | No. 6 | 23.3 | 36.5 | 57.8 | 87.9 | 101.8 |
| | | 23.9 | 38.5 | 59.9 | 87.9 | 101.0 |

Figure 4:
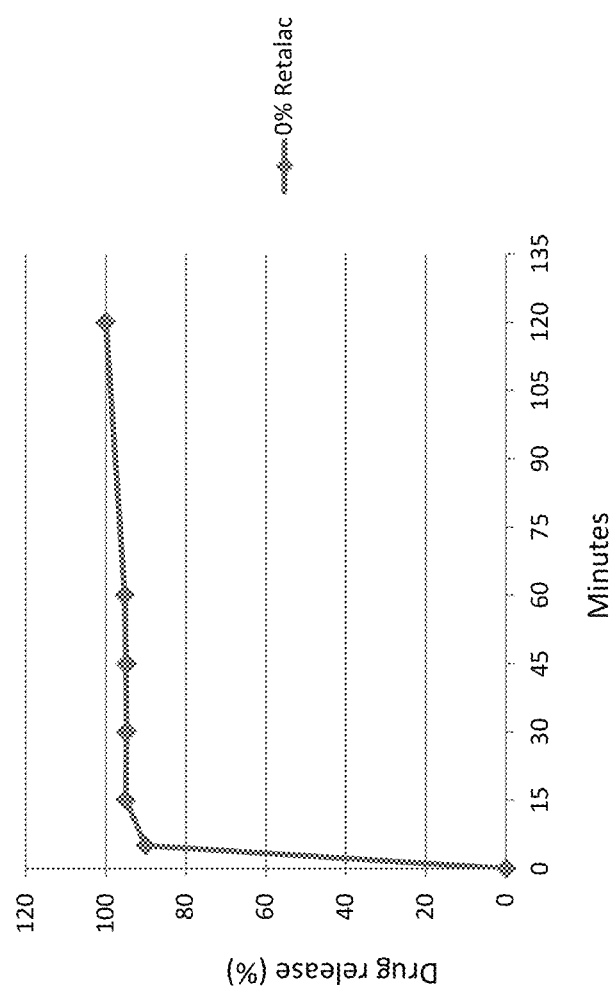
FIG. 4 shows the dissolution profile for a colchicine sustained-release formulation containing 0% of an exemplary retarding agent.

The dissolution profile for Batch 5 is summarized in Table 6 and FIG. 4. Batch 5 represents the immediate release version of the composition. The profile for Batch 5 shows a 90% release within 5 minutes. Complete dissolution occurred within 2 hours.

TABLE 6

| Concentration Retardant | Sample | min 0 | min 5 | min 15 | min 30 | min 45 | min 60 | min 120 |
|---|---|---|---|---|---|---|---|---|
| 0% Retalac | 1 | | 92.2 | 96.8 | 96.8 | 96.9 | 97.2 | |
| | 2. | | 96.7 | 100.6 | 99.9 | 100.3 | 100.7 | |
| | 3. | | 94.7 | 100.8 | 100.5 | 100.9 | 101.1 | |
| | 4. | | 86.5 | 92.7 | 92.9 | 93.1 | 93.3 | |
| | 5. | | 85.6 | 91 | 91.7 | 91.4 | 91.8 | |
| | 6. | | 84.5 | 88.1 | 87.1 | 87.1 | 87.5 | |
| | Mean | 0 | 90.0 | 95.0 | 94.8 | 95.0 | 95.0 | 100 |

Table 7 below summarizes another batch, Batch 6, that was tested.

| Material name | Mass [%] | Mass per Tbl. [mg] | Per batch [g] | Range for variation | Weighting Tolerance |
|---|---|---|---|---|---|
| PE Colchicine | 0.550 | 0.550 | 5.5 | | 0.5% |
| Lactose monohydrate EP | 58.950 | 58.950 | 589.50 | | 1% |
| Pregelatinized Starch USP | 7.500 | 7.500 | 75.00 | | 1% |
| FB Hypromellose 6 mPa * s EP/JP/USP | 1.000 | 1.000 | 10.00 | | 1% |
| Water purified * for Colchicine | 0.000 | 4.000 | 40.00 | | 1% |
| Water purified * For Hypromellose | 0.000 | 8.300 | 83.00 | | 1% |
| Tableting mix 25% Retalac (compression strength = 55N): | | | | | |
| Lactose monohydrate EP (Filling agent ad 100 mg per tablet) | 5.00 | 5.00 | 50.00 | 2.5% 10% | 1% |
| PE Retalac (50% Lactose/ 50% Hypromellose 4000 mPas) | 25.00 | 25.00 | 250.00 | 20% 27.5% | 1% |
| Talc EP/JP | 1.000 | 1.000 | 10.00 | | 1% |
| Stearic acid 50 EP | 1.000 | 1.000 | 10.00 | | 1% |
| Total tablet weight: | 100.000 | 100.000 | 1,000.00 | | |
| Related Substances | NMT 2.5% | | | | |
| N-Deacetyl-N-formyl-Colchicine (imp A) | NMT 1% | | | | |
| unknown impurities | NMT 3.5% | | | | |
| Total impurities | | | | | |

Figure 5:
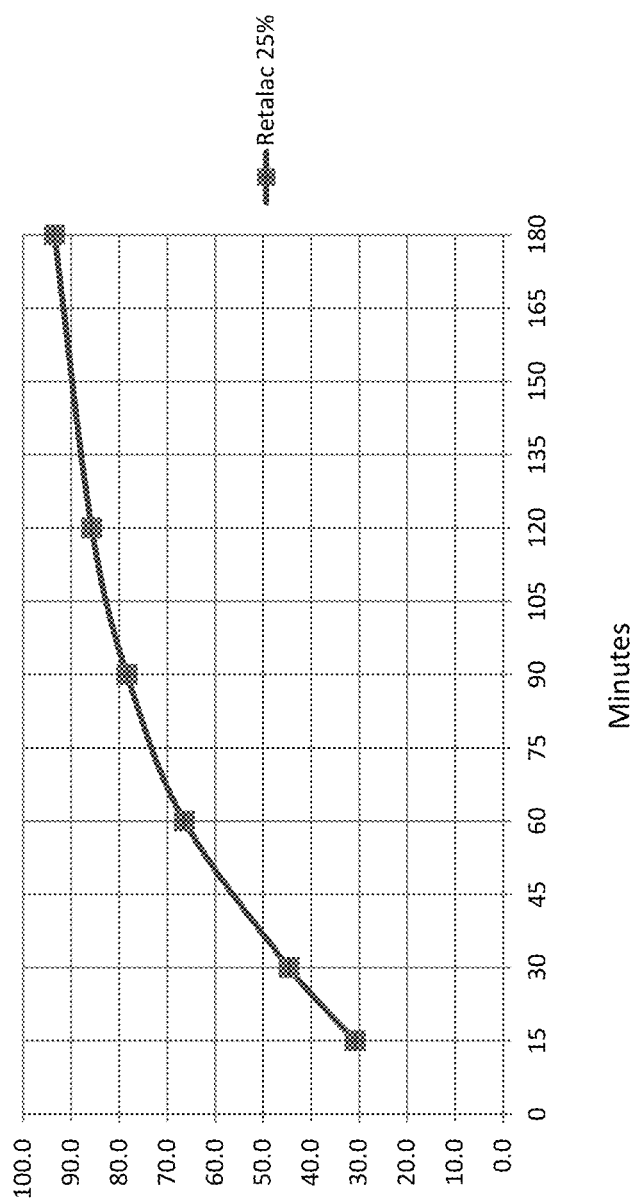
FIG. 5 shows the dissolution profile for a colchicine sustained-release formulation containing 25% of an exemplary retarding agent.

The dissolution profile for Batch 6 is summarized in FIG. 5. Batch 6 represents a sustained release version of the composition. The profile for Batch 6 in FIG. 5 shows about a 45% release within 30 minutes, about a 65% release in 60 minutes, and about a 80% release in 90 minutes. Complete dissolution occurs within about 2 hours.

Figure 6:
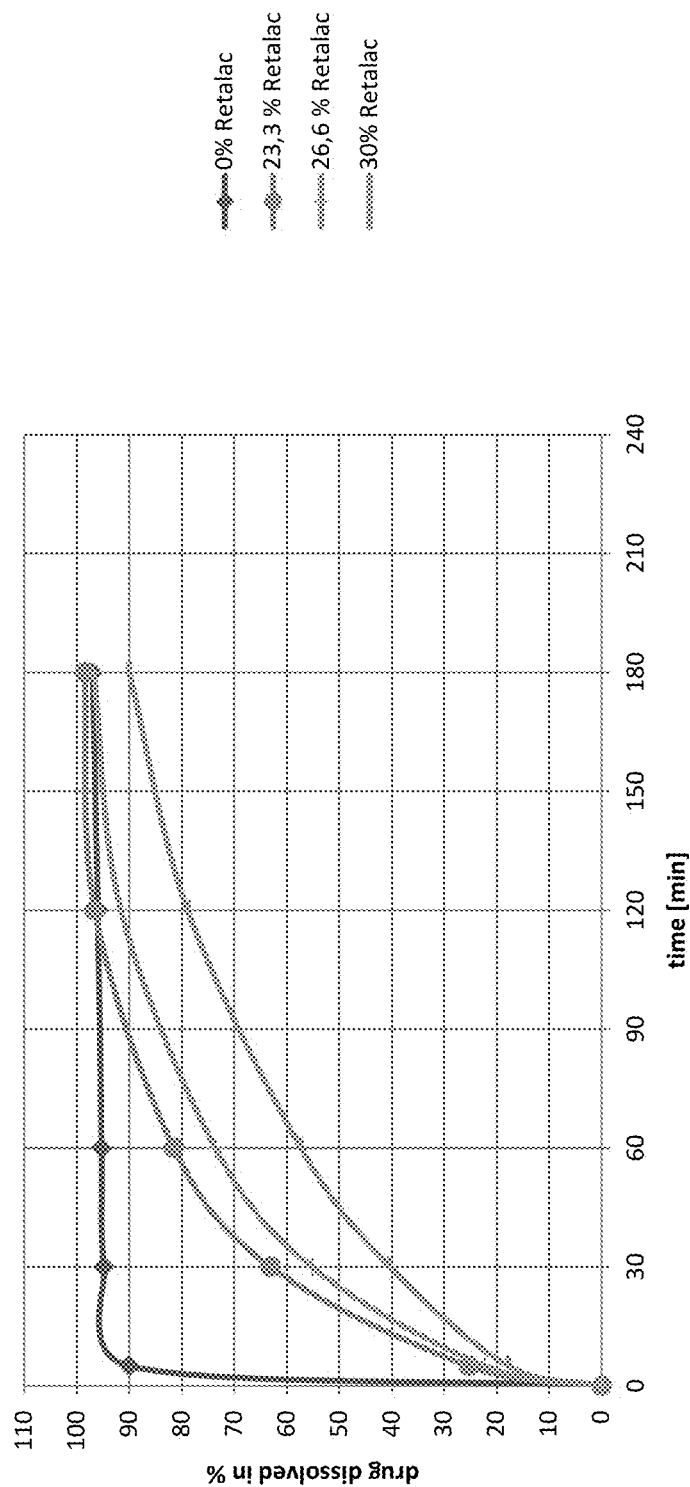
FIG. 6 shows the dissolution profile for colchicine formulation containing 0%, 23.3%, 26.6% and 30% of an exemplary retarding agent.

Batch 4 was further modified by altering the concentration of retarding agent (i.e. Retalac) in the composition (Retalac 0%, 23.3%, 26.6% or 30%). The dissolution profiles of the four compositions are shown in FIG. 6. As shown in FIG. 6, the composition with 23.3% Retalac shows about a 65% release within 30 min, about a 80% release in 60 min, and about a 90% release in 90 min. Complete dissolution occurs within about 120 min. As further shown in FIG. 6, the composition with 26.6% Retalac shows about a 55% release within 30 min, about a 75% release in 60 min, and about a 85% release in 90 min. Complete dissolution occurs within about 180 min. As further shown in FIG. 6, the composition with 30% Retalac shows about a 40% release within 30 min, about a 55% release in 60 min, and about a 70% release in 90 min. Complete dissolution occurs in more that about 180 min. As further shown in FIG. 6, the composition with 0% Retalac (i.e., immediate release composition) shows complete dissolution within about 15 min.

As mentioned previously, the release profile of the sustained release composition can be changed to a specific or desired target release by adjusting the amount of retarding agent (i.e., Retalac) as well as tablet hardness. The release depends upon a variety of factors, including erosion of the outer layer of colchicine (i.e., the immediate release portion) as well as diffusion of the inner layer of colchicine (i.e., the sustained release portion). Since the percentage of colchicine is low in the sustained release formulation and the tablets are small, this balance between erosion and diffusion is very sensitive and has to be fine-tuned to reach a very specific dissolution profile.

Example 4: Measurements of Dissolution Profiles of Sustained-Release Colchicine Formulations in Ethanol To assess the potential for dose dumping, or dissolution of the composition in alcohol, the dissolution of the sustained release formulation of colchicine in ethanol was measured at various time points. The compositions were dissolved in 500 ml of three solutions, 5%, 20% and 40% ethanol, at 37° C. and stirred continuously over a period of 6 hours. Samples were drawn at several time points to study the kinetics of the dissolution process of the drug substance within the hydrophilic matrix system. Colchicine content in the samples was analyzed using HPLC analysis.

Example 5: Pharmacokinetic Properties of Sustained-Release Colchicine Formulations The therapeutic effect of the sustained release formulation containing of colchicine is evaluated in a clinical study that is a multidose, randomized, cross-over study, which will evaluate bioavailability of about 3 different 0.50 mg sustained release formulations (e.g. Test Products 1,2,3 and FIG. 6) of colchicine to a 0.5 mg immediate release formulation (control product), administered to healthy volunteers. Test products 1, 2, and 3 used varying levels of retarding agent (i.e., Retalac), 23.3%, 26.6% or 30%, respectively, thereby having different sustained release profiles. The primary aim of the study is to assess pharmacokinetics (PK) of test and control drug in blood as well as in neutrophils or leucocytes.

Research Objective:

The primary objective of this study is to compare the pharmacokinetics of the test product vs. control product of colchicine in healthy human volunteers. In particular, levels of colchicine in blood (herein referred as to blood PK), neutrophils or leucocytes (herein referred as to neutrophil PK) will be assessed upon treatment with control and test product.

The hypothesis tested is that administration of an equal amount of colchicine in form of a sustained release tablet leads to lower peak levels (Cmax), while maintaining equal absolute bioavailability (area under the curve, AUC). Colchicine concentrations in neutrophils are measured as it is generally recognized that neutrophils which reconstitute 60-70% of leukocytes, play a central role in inflammatory responses in general and are thought to be major players in several diseases where colchicine is used as treatment. Therefore for the purpose of this experiment, either leucocytes or neutrophils may be analyzed. Hence, the term neutrophils as used herein also refers to, if used, leucocytes. As colchicine is known to preferentially accumulate in neutrophils and inhibit many of their pro-inflammatory functions, they are thought to be a major target of colchicine therapy. Therefore it is of special interest to know whether similar concentrations of colchicine are reached in isolated neutrophils or in leukocytes which would give information on potential bioequivalence. Therefore, blood will be drawn in various time points over the course of the study to check colchicine concentrations in blood and neutrophils.

General Study Design:

This study is designed as a randomized, cross-over study. There will be 3 groups of patients (n=3× at least 8). Group 1 will receive control or test drug for about 8-14 days. After a wash out period, they will receive test drug 1 for about 8-14 days. Group 2 will receive the control drug for the same time. After a wash out period, they will receive test drug 2 for the same time. Group 3 will receive the control drug for the same time. After a wash out period, they will receive test drug 3 for the same time. The study participants are treated on an in-patient basis for the first 24 h and on an out-patient basis for the remaining time. A sufficiently long wash-out period lies between the two trials.

Subject Participation:

There will be 3 groups of patients (n=3× at least 8). For each test drug, healthy volunteers will be randomized to one drug for the first round. After a sufficient wash out period, the same subjects will receive the control drug.

Study Duration:

The study drug is administered at a single dose/day for about 8-14 days consecutive days. The study consists of 24 h blood PK (high frequency data collection). Neutrophil PK is analysed in intervals that allow for conclusive determination of colchicine levels in the latter over the duration of the experiment.

Treatment Regimen:

Below is an example of what the treatment regime may look like.

|  | Cycle 1 | Wash out | Cycle 2 |
| --- | --- | --- | --- |
| Group 1 | 14 days Control or test 1 | 14 days | 14 days Test 1 or control |
| Group 2 | 14 days Control or test 2 | 14 days | 14 days Test 2 or control |
| Group 3 | 14 days Control or test 3 | 14 days | 14 days Test 3 or control |

Research Techniques and Data Analysis:

Analytical chemistry techniques (HPLC) or immunological techniques (radioimmunoassay) may be utilized for the assessment of colchicine and optionally, its metabolites. Collected data is analyzed by adequate data management and statistics software.

Subject Population:

The study population consists of male healthy volunteers (n=5-10/group). For inclusion in the study, the patient must be 25-40 years of age; not less than 60 kg and not more than 120 kg body weight; healthy; no major competing comorbidities or contraindication to colchicine therapy; willing to provide consent and be randomized into the study. Patients who meet the following criteria will be excluded: ongoing therapy with other anti-inflammatory/immunosuppressive drugs; treatment with drugs with known drug interactions with colchicine; renal/hepatic impairment; known hypersensitivity to colchicine.

Treatment Schema:

The drug is given once a day in the morning.

Data Collection Schema:

For blood PK, blood will be collected over a period of 24 h at the beginning the study in short intervals (sufficient time points to establish pharmacokinetic data, e.g.: −1, +0.5 h, 1 h, 1.5 h, 2 h, 3 h, 4 h, 5 h, 7 h, 10 h, 12 h, 15 h and 24 h (before next application). Additional time points may be 24 h, and 10 days after drug withdrawal at the end of the study to examine the wash out phase of the drug. PK analysis includes colchicine blood concentrations. Adequate techniques for the isolation of blood and quantification of colchicine are applied.

For neutrophil PK, neutrophils will be isolated or purified from raw blood from several time points. Neutrophils will be collected at the beginning the study as well as at least once at the end of the study. PK analysis includes colchicine concentrations in isolated neutrophils.

Figures 7A, 7B, 7C, 7D:
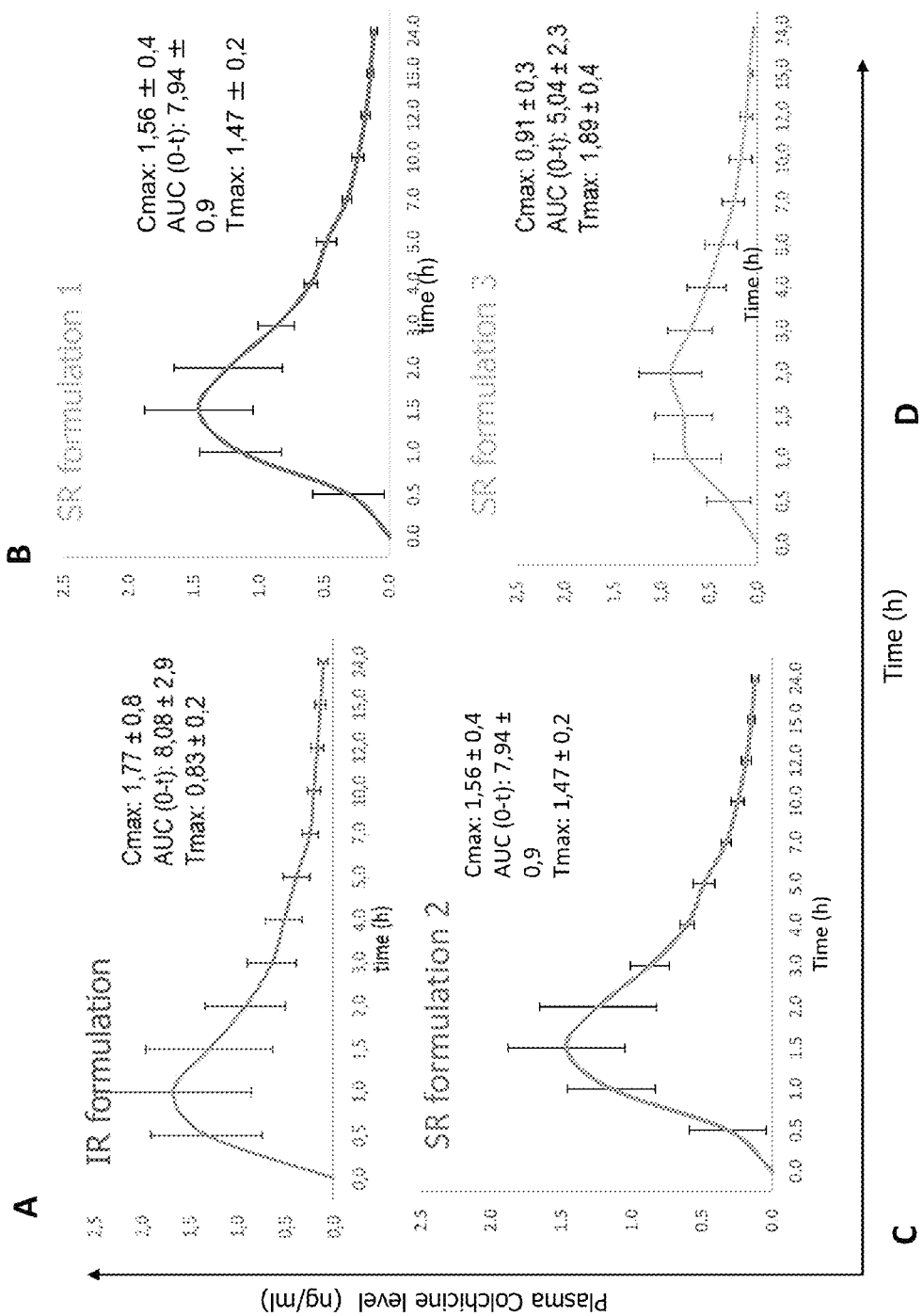
FIGS. 7A, 7B, 7C and 7D show plasma colchicine levels (ng/mL) as a function of time (hrs) for colchicine formulations according to FIG. 6.
Figure 8:
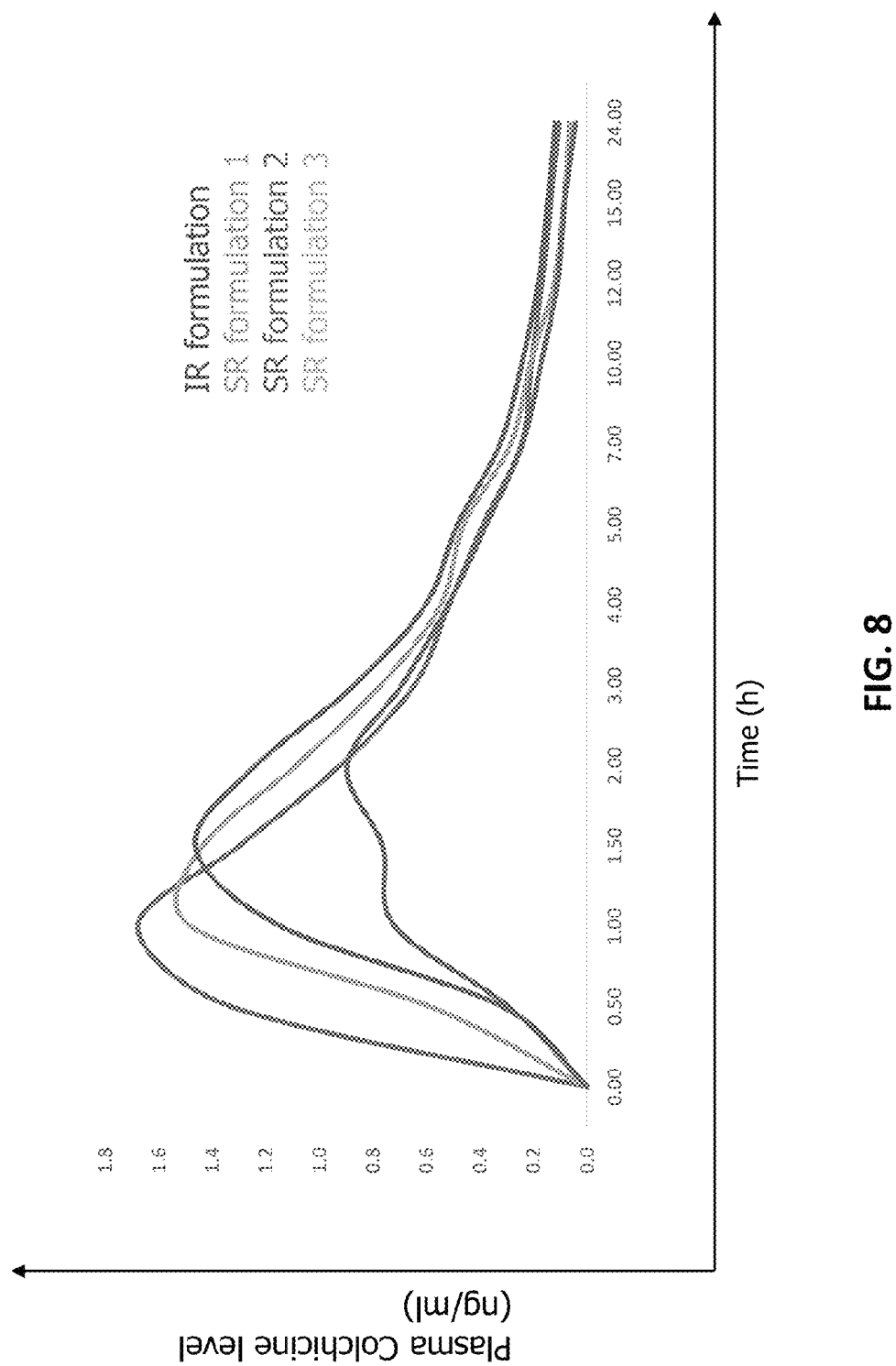
FIG. 8 shows plasma colchicine levels (ng/mL) as a function of time (hrs) for colchicine formulations according to FIG. 6.
Figure 9:
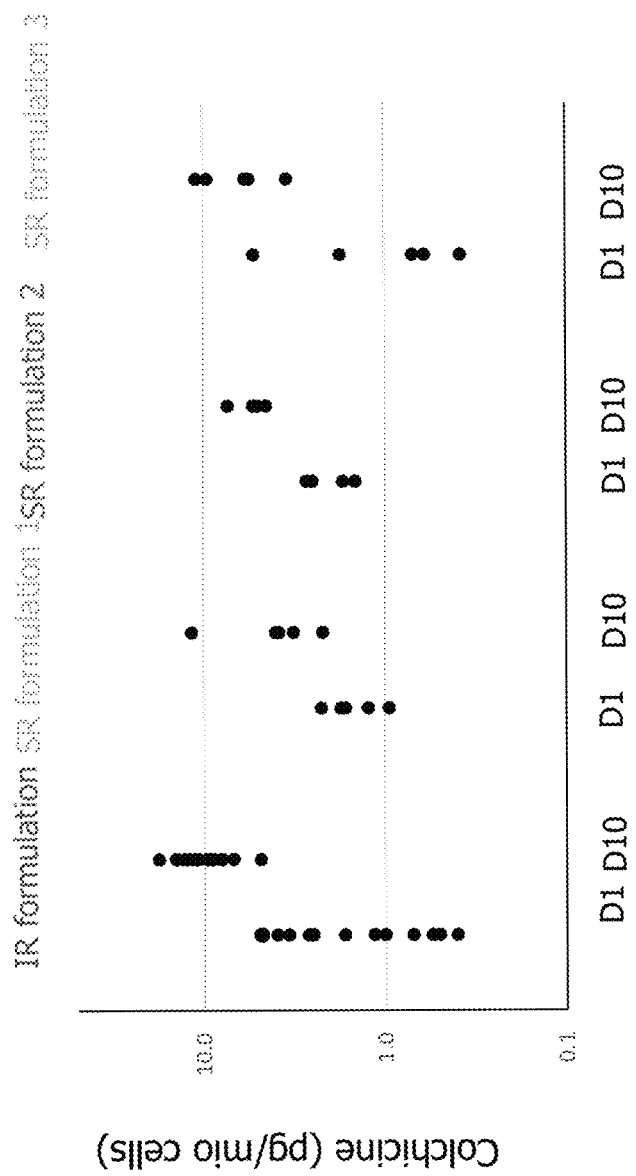
FIG. 9 shows the levels of colchicine in neutrophils on Day 1 and Day 10 for colchicine formulations according to FIG. 6.

Results: The results are shown in FIGS. 7-9. FIGS. 7A, 7B, 7C and 7D show plasma colchicine levels (ng/mL) as a function of time (hrs) in the immediate release formulation (FIG. 7A) as compared to the sustained release formulations (FIGS. 7B, 7C and 7D). The immediate release formulation of FIG. 7A has a Cmax of 1.77+/−0.8 ng/mL, an AUC (o-t) of 8.08+/−2.9 ng/mL and a Tmax of 0.83+/−0.2 hr. The sustained release formulation of FIG. 7B has a Cmax of 1.56+/−0.4 ng/mL, an AUC (o-t) of 7.94+/−0.9 ng/mL and a Tmax of 1.47+/−0.2 hr. The sustained release formulation of FIG. 7C has a Cmax of 1.56+/−0.4 ng/mL, an AUC (o-t) of 7.94+/−0.9 ng/mL and a Tmax of 1.47+/−0.2 hr. The sustained release formulation of FIG. 7D has a Cmax of 0.91+/−0.3 ng/mL, an AUC (o-t) of 5.04+/−2.3 ng/mL and a Tmax of 1.89+/−0.4 hr. FIG. 8 shows the overlapping profiles of the immediate release formulation and the three sustained release profiles. As can be seen, there is less inter-subject variation in plasma levels, lower Cmax and similar AUC for the sustained release formulation of FIG. 7B when compared to the immediate release formulation. Since the colchicine concentration on plasma increases and decreases more steadily and in a more controlled way, and the variability of colchicine levels in plasma from patient to patient is less, the safety and efficacy profile is more predicable. As a result, there will likely be fewer adverse side effects (e.g., gastrointestinal side effects) and/or reduced risk of toxicity (e.g., due to drug-drug interactions or co-morbidities such as renal and/or hepatic impairment).

FIG. 9 shows the levels of colchicine in neutrophils on Day 1 and Day 10 in the immediate release formulation and the three sustained release formulations. As can be seen, the levels of colchicine increase from Day 1 to Day 10, suggesting that colchicine accumulates in neutrophils over time. The results further show that the levels in neutrophils are similar after 10 days regardless of the formulation, suggesting that the therapeutic effect will be equal for the tested sustained release and immediate release formulations (as the site of action of colchicine is neutrophils).

Example 6: Therapeutic Effects of an Immediate Release Formulation in Patients with Cardiovascular Disease To assess the therapeutic effects of an immediate release formulation in patients with cardiovascular disease, a prospective randomized observer blinded end-point trial was conducted to determine whether adding 0.5 mg/day of colchicine to standard secondary prevention therapies including aspirin and high dose statins reduces the risk of cardiovascular events in patients with objectively diagnosed and clinically stable coronary disease. This study is described in PCT/AU2013/001261 and is hereby incorporated in its entirety by reference.

Study Conduct and Design:

The LoDoCo Trial was conducted under the auspices of the Heart Research Institute of Western Australia. It was designed by the principal investigators, registered with the Australian Clinical Trial Registry (12610000293066), and received ethics approval from the Human Research Ethics Committee at Sir Charles Gairdner Hospital Perth Western Australia in July 2008. There was no external funding source.

The study had a prospective randomized, open, blinded end-point design. Eligible consenting patients with established coronary disease presenting for routine clinical review were randomized to receive colchicine 0.5 mg/day or no colchicine without any other change to their medical therapy. All outcomes were evaluated by an experienced adjudicator blinded to the treatment allocation.

Study Size and Eligibility:

It was planned to recruit a study population that would include 250 patients, 28 randomized to the control group and 250 patients randomized to treatment who were tolerant of colchicine for at least 4 weeks after the date of their randomization. Patients were eligible for inclusion if they met each of the following criteria: 1) angiographically proven coronary disease; 2) aged 35 to 85 years; 3) clinically stable for at least 6 months, 4) no major competing co-morbidities or contraindication to colchicine therapy, 5) considered to be compliant with therapy and attending routine cardiology follow up appointments, and 6) willing to be consented and randomized into the study. Patients with a history of bypass surgery were only eligible if they had undergone bypass surgery more than 10 years before, or had angiographic evidence of graft failure or had undergone stenting since their bypass surgery. All patients signed informed consent before randomization.

Randomization:

The randomization sequence was computer generated, kept concealed from the investigators at all times and was managed by a research assistant who had no involvement in the evaluation or management of study patients. Once the assistant received the consent form, the patients' demographic data were entered into the data base and the investigators and patients were advised in writing of the treatment group to which the patient had been assigned. Despite electing to use the lowest dose of colchicine available, it was anticipated that a number of patients would withdraw from therapy early after randomization due to gastrointestinal side effects. In order to ensure that the requisite number of patients in the treatment arm were actually tolerant of treatment, the protocol allowed for the research assistant to assign a newly recruited patient to treatment if a patient discontinued colchicine due to side effects in the first month. Patients who were intolerant to therapy remained in the study, and were followed in the usual manner and included in the primary intention to treat analysis.

Intervention:

Patients randomized to active treatment were given a prescription for colchicine 0.5 mg daily by their referring cardiologist. The drug was dispensed by their usual chemist, and if requested, patients were reimbursed for the cost of these scripts. All other treatments were continued as usual.

Follow-Up and Definition of Clinical Outcomes:

Patient compliance with treatment and outcome data were collected at routine follow up visits and at the time of any unplanned hospital admission. An acute coronary syndrome (ACS) was defined as either (a) Acute Myocardial Infarction (AMI), as evidenced by acute ischemic chest pain associated with a rise in serum troponin above the upper limit of normal or (b) Unstable Angina (UA), as evidenced by a recent acceleration of the patient's angina unassociated with a rise in serum troponin but associated with angiographic evidence of a change in the patient's coronary anatomy. (Unstable Angina Braunwald classification types IB and IIB). The ACS was characterized as being stent-related if there was evidence of significant in-stent stenosis or acute stent thrombosis. Out of Hospital Cardiac Arrest was defined as either a sudden death as evidenced on the patient's death certificate, or a non-fatal out of hospital cardiac arrest, defined as a recovery from sudden collapse associated with documented asystole, ventricular tachycardia or ventricular fibrillation. Noncardioembolic ischemic stroke was defined as CT or MRI proven ischemic stroke adjudged by the treating neurologist as not being due to atrial fibrillation or intracranial hemorrhage.

The primary efficacy outcome was the composite, ACS, fatal or non-fatal out of hospital cardiac arrest or non-cardio-embolic ischemic stroke. Secondary outcomes were (a) individual components of the primary outcome, and (b) the components of ACS unrelated to stent disease.

Timelines:

The pre-specified study duration was a minimum follow up of two years in all patients. Accordingly the study was closed on May 31, 2012. During May, all living patients were contacted by phone to collect compliance and outcome data from the last date of follow-up. Final outcome data were available in all patients and no patients were lost to follow up.

Statistical Power:

Assuming that the control group had a combined event rate (ACS, out of hospital cardiac arrest or non cardio-embolic-ischemic stroke) of 8%, an accrual interval of 2 years and a follow-up after the accrual interval of 2 years, the planned sample size provided >80% power to detect a hazard ratio of <0.50 based on a two sided significance level of 5%.

Data Analysis:

Summary statistics, including mean and standard deviation were calculated for all baseline characteristics by treatment arm. All time to event outcomes were calculated in days by subtracting the date of randomization from either: (1) the date of event or death; or (2) the trial termination date for those patients not experiencing the defined event. As pre-specified, the primary efficacy analysis was based on the intention-to-treat principle. The intention-to-treat analysis included all randomized subjects and all events during the time from randomization to the trial termination. Trial termination date was fixed as May 31, 2012. A secondary pre-specified on-treatment analysis was also performed, based on patients who were both tolerant and compliant to therapy beyond the first month of randomization. All events during the time from randomization until non-compliance with colchicine treatment regimen were included in this analysis.

The time-to-first-event for all outcomes is presented using a Kaplan-Meier plot. The primary efficacy outcome was analyzed using a cox proportional hazards model including treatment group coded as control or colchicine. The secondary outcomes were analysed similarly. In addition, the primary analysis was stratified by gender, age, diagnosis of diabetes, past myocardial infarction, unstable angina, coronary bypass surgery, coronary angioplasty, and therapy with aspirin, clopidogrel or both, high dose statin therapy (defined as a dose of statin equivalent to atorvastatin of 40 mg or more), beta blockers, calcium blockers and ACE inhibitors.

Results:

Between August 2008 and May 2010, 901 patients with stable coronary disease attending for routine out-patient cardiology review were assessed for eligibility for the study. Of these, 297 (33%) did not meet the entry criteria, 72 (8%) declined to participate and 532 (59%) were enrolled into the study, 250 of whom were randomized to the control group and 282 to treatment. Of those randomized to treatment 32 (11%) reported early intolerance, due to gastrointestinal side effects, and 7 patients subsequently reported that they chose not start therapy. All 532 randomized patients were followed for the duration of the study period which ranged from a minimum of 24 to a maximum of 44 months. Median follow up was 36 months.

Outcomes:

A primary outcome occurred in 55/532 patients, including 15/282 (5.3%) patients assigned to colchicine treatment, and 40/250 (16%) patients assigned to the control group [hazard ratio 0.33, 95% CI; 0.18-0.59; p<0.001, number needed to treat 11). A sensitivity analysis was performed for the primary outcome, adjusting for the usage of calcium channel blockers and beta blocker therapy. These results were consistent with the primary analysis.

The effect of colchicine on the primary outcome was evident early and the benefits of colchicine continued to accrue throughout the follow up period. There was no evidence of differential treatment effects based on any of the clinical or therapeutic variables.

The reduction in the primary outcome was largely driven by the reduction in the number of patients presenting with an ACS, (13/282 (4.6%) vs. 34/250 (13.4%), hazard ratio 0.33; 95% CI; 0.18-0.63; p<0.001). Out of hospital cardiac arrest and non-cardio-embolic ischemic stroke were infrequent but were also reduced in the treatment group.

Of the 47 patients who presented with an ACS, the event was stent related in 8 (17%) (2 in each group had evidence of acute stent thrombosis and 2 in each group had evidence of significant in-stent stenosis). Further analysis confirmed that patients randomized to treatment were less likely to present with an ACS unrelated to stent disease (9/282 (3.2%) vs. 30/250 (12%) hazard ratio 0.26, 95% CI; 0.12-0.55; p<0.001), be it associated with an AMI (4/282 (1.4%) vs. 14/250 (5.6%) hazard ratio 0.25, 95% CI; 0.08-0.76; p=0.014) or UA (5/282 (1.8%) vs. 16/250 (6.4%) hazard ratio 0.27, 95% CI; 0.10-0.75; p=0.011).

Of 39 patients randomized to treatment who did not receive therapy beyond the first month due to early intolerance or non-compliance, 4 (10%) presented with an ACS due to acute stent thrombosis (n=1) and UA (n=3). Patients who were both compliant and tolerant to therapy beyond the first month of randomization had significantly fewer events than the control patients (11/243 (4.5%) vs. 40/250 (16%) hazard ratio 0.29, 95% CI; 0.15-0.56; p<0.001). The results of all on-treatment analyses were consistent with those based upon the intention to treat analyses.

Ten patients in the control group died compared with 4 patients in the colchicine group. Of the 10 controls, 5 died of presumed cardiac cause; 2 following an out-of-hospital cardiac arrest, 2 from cardiogenic shock following myocardial infarction, and 1 following bypass surgery. All 4 patients in the colchicine group died of non-cardiac causes.

This trial demonstrates that the addition of colchicine 0.5 mg/day to standard therapy in patients with stable coronary disease significantly reduces the risk of a cardiovascular event, including an ACS, out of hospital cardiac arrest and non-cardio-embolic ischemic stroke. The benefits of colchicine were achieved on a background of widespread use of effective secondary prevention strategies, including high dose statins, as evidenced by the low event rate in the control group. The effect of adding colchicine became evident early, continued to accrue over time and was largely driven by a reduction in ACS unrelated to stent disease.

Example 7: Dose Adjustments of Sustained Release Colchicine Formulations

To determine the proper dose amounts, the sustained released formulation may be administered to patient populations with different body weights. Assuming that a 0.5 mg tablet gives a certain plasma level of colchicine in average weight patients and that this particular level should be reached in every patient to achieve efficacy, one can perform PK analysis of a 0.5 mg tablet in different weight groups. It is expected that levels in blood (Cmax and AUC) in heavy patients are lower, which indicates that dose adjustments towards higher doses is necessary.

Research Objective:

The primary objective of this study is to compare the pharmacokinetics of a 0.5 mg colchicine tablet in healthy human volunteers of at least 2 different body weight groups. In particular, levels of colchicine in blood will be assessed upon treatment. The hypothesis tested is that administration of an equal amount of colchicine in leads to different colchicine levels depending to body weight. Body weight and colchicine levels are inverse correlated.

General Study Design:

This study is designed as a randomized, cross-over study. n=at least 8 subjects are selected according to body weight. If 2 groups are made, then 50% will be of low weight (e.g. below 65 kg) and 50% of high weight (e.g. above 90 kg).

Study Duration:

The study drug is administered once. The study consists of 24 h blood PK (high frequency data collection).

Research Techniques and Data Analysis:

Analytical chemistry techniques (HPLC) or immunological techniques (radioimmunoassay) may be utilized for the assessment of colchicine. Collected data is analyzed by adequate data management and statistics software.

Subject Population:

The study population consists of male healthy volunteers. For inclusion in the study, the patient must be 25-40 years of age; not less than 50 kg and not more than 120 kg body weight; healthy; no major competing comorbidities or contraindication to colchicine therapy; willing to provide consent and be randomized into the study. Patients who meet the following criteria will be excluded: ongoing therapy with other anti-inflammatory/immunosuppressive drugs; treatment with drugs with known drug interactions with colchicine; renal/hepatic impairment; known hypersensitivity to colchicine.

Treatment Schema:

The drug is given once in the morning of the study.

Data Collection Schema:

For blood PK, blood will be collected over a period of 24 h at the beginning the study in short intervals (sufficient time points to establish pharmacokinetic data, e.g: −1, +0.5 h, 1 h, 1.5 h, 2 h, 3 h, 4 h, 5 h, 7 h, 10 h, 12 h, 15 h and 24 h (before next application). Additional time points may be 24 h, and 72 h after drug withdrawal at the end of the study to examine the wash out phase of the drug.

Example 8: Non-Clinical Pharmacokinetics Study of Sustained Release (SR) Versus Immediate Release (IR) of Colchicine A sufficiently high number of adequate laboratory animals (e.g. rodents such as mice or rats, at least 5 animals per group) is used in this experiment. The control drug is an IR tablet of colchicine. The test drug is an SR tablet of colchicine.

The control group of mice is given a single first dose of IR colchicine in a strength which lies in the therapeutic window (the plasma level range of colchicine where a therapeutic effect can be observed. It will be determined and set arbitrary in the used laboratory animal species as a maximum level sufficiently below the LD50 and a minimum level approximately 6 fold less than the maximum level). The test group is given a single first dose of SR colchicine in the same strength. Blood is drawn from both groups at time points 0.25 h, 0.5 h, 0.75 h, 1 h, and then hourly for 12 h and every 3 hours until 24 h. Simultaneously, feces are drawn from the cages of test and control animals after 3 h, 6 h, 12 h and 24 h (test and control animals must not be put in the same cages).

Primary readout: Colchicine plasma levels. Secondary readout: Determination of colchicine and its metabolites in feces to see whether enterohepatic recirculation occurs to a lesser extent in test animals than in control animals. Blood samples are processed and colchicine levels in blood plasma are measured with HPLC analysis or an equivalent quantitative method.

Results: The experiment is expected to show that the total absorption of colchicine (area under the curve) is similar in test and control animals. However, in control animals, colchicine absorption peaks at ca. 1 h post administration and then rapidly declines. After 2-3 h, colchicine levels are below the therapeutic range. Also, due to enterohepatic recirculation of un-metabolized colchicine, re-absorption occurs which manifests in the characteristic secondary peak after 3-6 h.

However, in test animals (SR), colchicine levels will rise more slowly and do not reach peak levels of colchicine as observed in control animals. The peak levels are observed after 3-8 h and then slowly decline. Therapeutic colchicine levels remain for at least 12 h. Due to the more complete metabolism of colchicine in the liver, enterohepatic recirculation occurs to a lesser extent and no secondary peak can be observed. As a secondary readout, feces of test and control animals are investigated to see whether enterohepatic recirculation occurs to a lesser extent in test animals than in control animals. It can be shown that the ratio of unchanged colchicine vs. metabolized colchicine is higher in control than in test animals. Thus, SR colchicine results in a more complete metabolism of colchicine in the liver.

Example 9: Non-Clinical Safety Study of SR Versus IR of Colchicine

A sufficiently high number of adequate laboratory animals (e.g. rodents such as mice or rats, at least 5 animals per group) is used in this experiment. The control drug is an IR tablet of colchicine. The test drug is an SR tablet of colchicine.

The control group of mice is given one dose IR colchicine/day in a strength which lies in the therapeutic window (the plasma level range of colchicine where a therapeutic effect can be observed. It will be determined and set arbitrary in the used laboratory animal species as a maximum level sufficiently below the LD50 and a minimum level approximately 6 fold less than the maximum level). The test group is given one dose SR colchicine/day in the same strength. Alternatively, test and control animals are given a total of two doses/day, one in the morning and one in the evening. The duration of the experiment is 2 weeks.

Primary readout is the incidence of gastrointestinal adverse events (e.g cramps, diarrhea etc.). This is evaluated in 3 ways. Daily, behaviour of the tested animals is observed with a predetermined standardized method where signs of illness are investigated. Secondly, feces are investigated daily for morphology as well as presence of apoptotic epithelial cells. Thirdly, individual animals are sacrificed at predetermined time points and the small and big intestine is investigated for histopathological signs of colchicine toxicity.

Results: Over the course of the experiment, it can be expected that the control animals suffer from more gastrointestinal adverse events than the test animals. Thus, SR colchicine exhibits a better safety profile than IR colchicine.

Example 10: Clinical Safety Study of SR Versus IR of Colchicine

If laboratory animals turn out to be inadequate for the investigation of adverse events related to colchicine administration, an equivalent experiment is carried out in humans. It is carried out in healthy adult volunteers or additionally in patients in need of colchicine. A sufficiently high number of humans is used to reach statistical significance. The test and control medication consists of a SR or IR oral solid dosage form of colchicine in strength of 0.25-1 mg. A sufficiently high dose is administered to reach therapeutic levels of colchicine. Alternatively to once daily administration, the tested drugs are given twice daily as indicated in Example 3, above. Alternatively, to control placebo effect, a placebo group is included in both experimental settings. The duration of the experiment is between 2 weeks and 1 month.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

What is claimed is:

1. A sustained release formulation of colchicine, comprising:
   (a) granules comprising colchicine or a pharmaceutically acceptable salt thereof in an amount of not more than 0.6 mg, and a binder comprising hydroxypropyl methylcellulose (HPMC) 6 mPa·s in an amount of 1% to 30% (w/w) of the formulation;
   (b) a release retarding agent admixed with, or blended with, the granules in an amount of between about 25% and about 30% w/w of the formulation, wherein the retarding agent comprises a combination of equal parts hydroxypropyl methylcellulose (HPMC) with a viscosity grade of 4000 mPa*s and lactose monohydrate; and
   (c) at least one additional pharmaceutically acceptable excipient admixed with or blended with the granules, wherein the at least one additional pharmaceutically acceptable excipient is starch, gelatin, polyvinylpyrrolidone (PVP), polyvinyl alcohol, microcrystalline cellulose, hydroxypropyl cellulose (HPC) or a mixture thereof,
   wherein the sustained release formulation is in a form of a tablet, and
   wherein the formulation is homogeneous.

2. The formulation of claim 1, wherein colchicine is included in an amount of about 0.55 mg.

3. The formulation of claim 1, wherein the compression strength of the tablet is between about 30N and about 130N.

4. The formulation of claim 1, wherein less than between about 23% and about 74% of colchicine is released in vitro into water within the first 120 minutes, or wherein less than about 70% of colchicine is released in vitro from said formulation within about 2 hours at 37° C.

5. The formulation of claim 3, wherein the compression strength of the tablet is between about 50N and about 130N.

6. The formulation of claim 3, wherein said compression strength is at least about 50N.

7. The formulation of claim 1, wherein the granules additionally comprise a first filling agent comprising lactose monohydrate in an amount of 10% to 80% (w/w) of the formulation, and wherein a second filling agent is admixed or blended with the granules, which comprises lactose monohydrate in an amount of 10% to 30% (w/w) of the formulation.

8. The formulation of claim 1, wherein less than about 70% of colchicine is released in vitro from said formulation within about 2 hours at 37° C.

9. The formulation of claim 1, wherein the sustained release formulation further comprises a filling agent, and wherein the filling agent is one or more of sucrose, lactose monohydrate, trehalose, maltose, mannitol, sorbitol, croscarmellose sodium, crospovidone, alginic acid, sodium alginate, methacrylic acid divinylbenzene (DVB), cross-linked PVP, polacrilin potassium, sodium starch glycolate, and pregelatinized starch.

10. A sustained release formulation of colchicine, comprising:
   (a) granules comprising colchicine or a pharmaceutically acceptable salt thereof in an amount of not more than 0.6 mg, and a binder comprising hydroxypropyl methylcellulose (HPMC) 6 mPa·s in an amount of 1% to 30% (w/w) of the formulation;
   (b) a release retarding agent admixed with, or blended with, the granules in an amount of between about 25% and about 30% w/w of the formulation, wherein the retarding agent comprises a combination of equal parts hydroxypropyl methylcellulose (HPMC) with a viscosity grade of 4000 mPa*s and lactose monohydrate; and
   (c) at least one additional pharmaceutically acceptable excipient admixed with or blended with the granules, wherein the at least one additional pharmaceutically acceptable excipient is starch, gelatin, polyvinylpyrrolidone (PVP), polyvinyl alcohol, microcrystalline cellulose, hydroxypropyl cellulose (HPC) or a mixture thereof,
   wherein the granules additionally comprise a first filling agent comprising lactose monohydrate in an amount of 10% to 80% (w/w) of the formulation, wherein a second filling agent is admixed or blended with the granules, which comprises lactose monohydrate in an amount of 10% to 30% (w/w) of the formulation, wherein the sustained release formulation is in a form of a tablet, and wherein the formulation is homogeneous.

11. The formulation of claim 10, wherein less than about 70% of colchicine is released in vitro from the sustained formulation within about 2 hours at 37° C.

12. The formulation of claim 10, wherein colchicine is included in an amount of about 0.55 mg.

13. The formulation of claim 10, wherein the compression strength of the tablet is between about 30N and about 130N.

14. The formulation of claim 10, wherein said compression strength is at least about 30N.

* * * * *